United States Patent
Omar et al.

(10) Patent No.: US 10,894,794 B1
(45) Date of Patent: Jan. 19, 2021

(54) SUBSTITUTED [1,2,4]TRIAZOLO[4,3-A]PYRAZINES AS ANTIDIABETICS

(71) Applicant: King Abdulaziz University, Jeddah (SA)

(72) Inventors: Abdelsattar M. Omar, Jeddah (SA); Mohamed A. El-Zahabi, Cairo (EG); Salah G. Atteiah, Zagazig (EG); Ashraf B. Abdel-Naim, Jeddah (SA); Moustafa E. El-Araby, Jeddah (SA)

(73) Assignee: King Abdulaziz University, Jeddah (SA)

(*) Notice: Subject to any disclaimer, the term of this patent is extended or adjusted under 35 U.S.C. 154(b) by 17 days.

(21) Appl. No.: 16/719,014

(22) Filed: Dec. 18, 2019

(51) Int. Cl.
- *A61K 31/4985* (2006.01)
- *C07D 487/04* (2006.01)
- *A61P 3/10* (2006.01)

(52) U.S. Cl.
CPC .............. *C07D 487/04* (2013.01); *A61P 3/10* (2018.01)

(58) Field of Classification Search
CPC .......................... A61K 31/4985; C07D 487/04
USPC .......................................... 514/249; 544/350
See application file for complete search history.

(56) References Cited

FOREIGN PATENT DOCUMENTS

CN     101357922    *   5/2011

* cited by examiner

*Primary Examiner* — Douglas M Willis
(74) *Attorney, Agent, or Firm* — W & C PC

(57) ABSTRACT

Compounds for the treatment of hyperglycemia and/or diabetes are provided. The compounds, which inhibit the enzyme dipeptidyl peptidase (DPP-4), are based on the structure Formula I

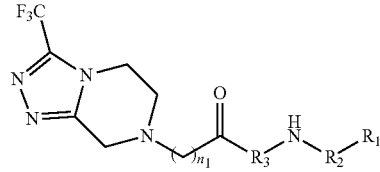

where n1=0-2 such as 0 or 1; R1 is i) a saturated or unsaturated, substituted or unsubstituted monocyclic aliphatic ring, alone or fused with cyclopropane or cyclobutene, optionally comprising one or more substituents attached to the ring; or ii) a substituted or unsubstituted monocyclic aromatic ring, optionally comprising one or more substituents attached to the ring; R2 is present or absent and if present is: C=O; $(CH_2)_n$ where n=0-4; S; SO; $SO_2$; NR where R=H, $CH_3$ or $CH_2CH_3$; or $NH(CH_2)_n$ where n=0-4; and R3 is present or absent and if present is $(CH_2)_n$ where n=0-4; S; SO; $SO_2$; NR where R=H, $CH_3$ or $CH_2CH_3$; or $NH(CH_2)n$ where n=0-4; and salts and isomers thereof.

16 Claims, 18 Drawing Sheets

SUBSTITUTED [1,2,4]TRIAZOLO[4,3-A]PYRAZINES AS ANTIDIABETICS

BACKGROUND OF THE INVENTION

Field of the Invention

The invention generally relates to new compounds for the treatment of hyperglycemia and/or diabetes. In particular, the compounds inhibit the enzyme dipeptidyl peptidase (DPP-4), and are used to prevent or treat Type II diabetes.

Description of Related Art

The dominance of Type 2 Diabetes Mellitus (T2DM) is increasing worldwide, especially in South Asia. India is the country with the highest diabetes incidence. The number of people with diabetes in India will reach 80 million by the year 2025 according to the International Diabetes Federation (IDF).

At least seven different classes of agents are used as monotherapy, or in combinations, for the treatment of diabetes mellitus. These classes are represented by metformin, sulphonylureas, meglinitides, alpha-glucosidase inhibitors, thiazolidinediones (TZD), glucagon like peptide-1 (GLP-1) agonists and insulin. Unfortunately, many of these agents exhibit reduced efficacy over time, leading to insufficient glycemic control. Some of these agents are also associated with adverse effects that include weight gain, hypoglycemia and gastrointestinal distress. Therefore, alternative therapies are needed to overcome the limitations associated with conventional anti-hyperglycemic medications.

SUMMARY OF THE INVENTION

DPP-4 inhibitors are of intense interest in the development of a new diabetes therapy and several are currently marketed (FIG. 1). The present disclosure provides new DPP-4 inhibitors that were developed by merging features of prior art inhibitors, vildagliptin, saxagliptin and sitagliptin. The new compounds exhibit high levels of DPP-4 inhibition and are used to treat, e.g. hyperglycemia and/or diabetes and related conditions.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of the present invention to provide a compound of generic structure

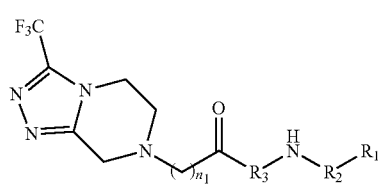

Formula I where $n_1$=0-2; R1 is i) a saturated or unsaturated, substituted or unsubstituted monocyclic aliphatic ring, alone or fused with cyclopropane or cyclobutene, optionally comprising one or more substituents attached to the ring; or ii) a substituted or unsubstituted monocyclic aromatic ring, optionally comprising one or more substituents attached to the ring; R2 is present or absent and if present is: C=O; $(CH_2)_n$ where n=1-4; S; SO; $SO_2$; NR where R=H, $CH_3$ or $CH_2CH_3$; or $NH(CH_2)_n$ where n=0-4; and R3 is present or absent and if present is $(CH_2)_n$ where n=1-4; S; SO; $SO_2$; NR where R=H, $CH_3$ or $CH_2CH_3$; or $NH(CH_2)n$ where n=0-4; and salts and isomers thereof. In some aspects, the one or more substituents are selected from the group consisting of: CN, OH, =O, $CH_3$, $CH_2CH_3$, isopropyl, cyclopropyl, $SO_2CH_3$, $SO_2NH_2$, $NH(CH_3)$, $N(CH_3)_2$, $NHCOCH_3$. In some aspects, R1 is cyclohexyl, R2 and R3 are absent and n=1 (GLP-140). In other aspects, R1 is phenyl, R2 is present, R3 is $CH_2$ and n=0 (GLP-136). In further aspects, R1 is phenyl with one or more substituents attached to the ring. In additional aspects, the one or more substituents includes CN, halogen or $OCH_3$. In some aspects, the halogen is F or Cl. In further aspects, the halogen is Cl. In some aspects, the Cl is at the meta position, R2 is present; R3 is $CH_2$ and n=0 (GLP 128). In further aspects, R2 is present; R3 is $CH_2CH_2$ and n=0 (GLP 129). In yet further aspects, R2 is present; R3 is $CH_2CH_3$ and n=0 (GLP 130). In additional aspects, the Cl is at the para position, R2 is present; R3 is $CH_2$ and n=0 (GLP 131). In other aspects, the one or more substituents is $OCH_3$, R2 is present; R3 is $CH_2$ and n=0 (GLP 138). In further aspects, the halogen is F, R2 is present; R3 is $CH_2$ and n=0 (GLP 139). In other aspects, the one or more substituents is CN, R2 is absent, R3 is absent and n=1 (GLP 142).

The disclosure also provides methods of preventing or treating hyperglycemia in a subject in need thereof, comprising administering to the subject a therapeutically effective amount of a compound of generic structure

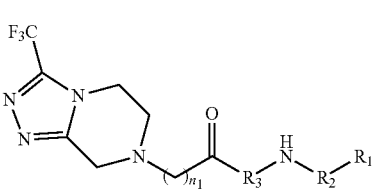

Formula I where $n_1$=0-2; R1 is i) a saturated or unsaturated, substituted or unsubstituted monocyclic aliphatic ring, alone or fused with cyclopropane or cyclobutene, optionally comprising one or more substituents attached to the ring; or ii) a substituted or unsubstituted monocyclic aromatic ring, optionally comprising one or more substituents attached to the ring; R2 is present or absent and if present is: C=O; $(CH_2)_n$ where n=1-4; S; SO; $SO_2$; NR where R=H, $CH_3$ or $CH_2CH_3$; or $NH(CH_2)_n$ where n=0-4; and R3 is present or absent and if present is $(CH_2)_n$ where n=1-4; S; SO; $SO_2$; NR where R=H, $CH_3$ or $CH_2CH_3$; or $NH(CH_2)n$ where n=0-4; and salts and isomers thereof. In some aspects, the one or more substituents are selected from the group consisting of: CN, OH, =O, $CH_3$, $CH_2CH_3$, isopropyl, cyclopropyl, $SO_2CH_3$, $SO_2NH_2$, $NH(CH_3)$, $N(CH_3)_2$, $NHCOCH_3$. In some aspects, R1 is cyclohexyl, R2 and R3 are absent and n=1 (GLP-140). In other aspects, R1 is phenyl, R2 is present, R3 is $CH_2$ and n=0 (GLP-136). In further aspects, R1 is phenyl with one or more substituents attached to the ring. In additional aspects, the one or more substituents includes CN, halogen or $OCH_3$. In some aspects, the halogen is F or Cl. In further aspects, the halogen is Cl. In some aspects, the Cl is at the meta position, R2 is present; R3 is CH$_2$ and n=0 (GLP 128). In further aspects, R2 is present; R3 is CH$_2$CH$_2$ and n=0 (GLP 129). In yet further aspects, R2 is present; R3 is CH$_2$CH$_3$ and n=0 (GLP 130). In additional aspects, the Cl is at the para position, R2 is present; R3 is CH$_2$ and n=0 (GLP 131). In other aspects, the one or more substituents is OCH$_3$, R2 is present; R3 is CH$_2$ and n=0 (GLP 138). In further aspects, the halogen is F, R2 is present; R3 is CH$_2$ and n=0 (GLP 139). In other aspects, the one or more substituents is CN, R2 is absent, R3 is absent and n=1 (GLP 142). 17. In some aspects, the subject has Type II diabetes. In further aspects, the compound is GLP 128, GLP129, GLP130, GLP131, GLP140 or GLP142.

The disclosure also provides methods of inhibiting dipeptidyl peptidase (DPP-4), comprising contacting the DPP-4 with at least one compound of generic structure

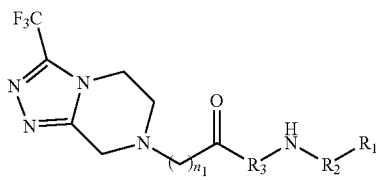

Formula I where
n$_1$=0-2; R1 is i) a saturated or unsaturated, substituted or unsubstituted monocyclic aliphatic ring, alone or fused with cyclopropane or cyclobutene, optionally comprising one or more substituents attached to the ring; or ii) a substituted or unsubstituted monocyclic aromatic ring, optionally comprising one or more substituents attached to the ring; R2 is present or absent and if present is: C=O; (CH$_2$)$_n$ where n=1-4; S; SO; SO$_2$; NR where R=H, CH$_3$ or CH$_2$CH$_3$; or NH(CH$_2$)$_n$ where n=0-4; and R3 is present or absent and if present is (CH$_2$)$_n$ where n=1-4; S; SO; SO$_2$; NR where R=H, CH$_3$ or CH$_2$CH$_3$; or NH(CH$_2$)n where n=0-4; and salts and isomers thereof. In some aspects, the one or more substituents are selected from the group consisting of: CN, OH, =O, CH$_3$, CH$_2$CH$_3$, isopropyl, cyclopropyl, SO$_2$CH$_3$, SO$_2$NH$_2$, NH(CH$_3$), N(CH$_3$)$_2$, NHCOCH$_3$. In some aspects, R1 is cyclohexyl, R2 and R3 are absent and n=1 (GLP-140). In other aspects, R1 is phenyl, R2 is present, R3 is CH$_2$ and n=0 (GLP-136). In further aspects, R1 is phenyl with one or more substituents attached to the ring. In additional aspects, the one or more substituents includes CN, halogen or OCH$_3$. In some aspects, the halogen is F or Cl. In further aspects, the halogen is Cl. In some aspects, the Cl is at the meta position, R2 is present; R3 is CH$_2$ and n=0 (GLP 128). In further aspects, R2 is present; R3 is CH$_2$CH$_2$ and n=0 (GLP 129). In yet further aspects, R2 is present; R3 is CH$_2$CH$_3$ and n=0 (GLP 130). In additional aspects, the Cl is at the para position, R2 is present; R3 is CH$_2$ and n=0 (GLP 131). In other aspects, the one or more substituents is OCH$_3$, R2 is present; R3 is CH$_2$ and n=0 (GLP 138). In further aspects, the halogen is F, R2 is present; R3 is CH$_2$ and n=0 (GLP 139). In other aspects, the one or more substituents is CN, R2 is absent, R3 is absent and n=1 (GLP 142). 17. In some aspects, the subject has Type II diabetes. In further aspects, the compound is GLP 128, GLP129, GLP130, GLP131, GLP140 or GLP142.

The complete contents of issued U.S. Pat. Nos. 6,395,767; 6,699,871; 7,375,238; 7,951,400 and 8,877,799, are hereby incorporated by reference in entirety. In some aspects, the compound is not a compound disclosed in any of U.S. Pat. Nos. 6,395,767; 6,699,871; 7,375,238; 7,951,400 and 8,877, 799.

DETAILED DESCRIPTION

Figure 1:
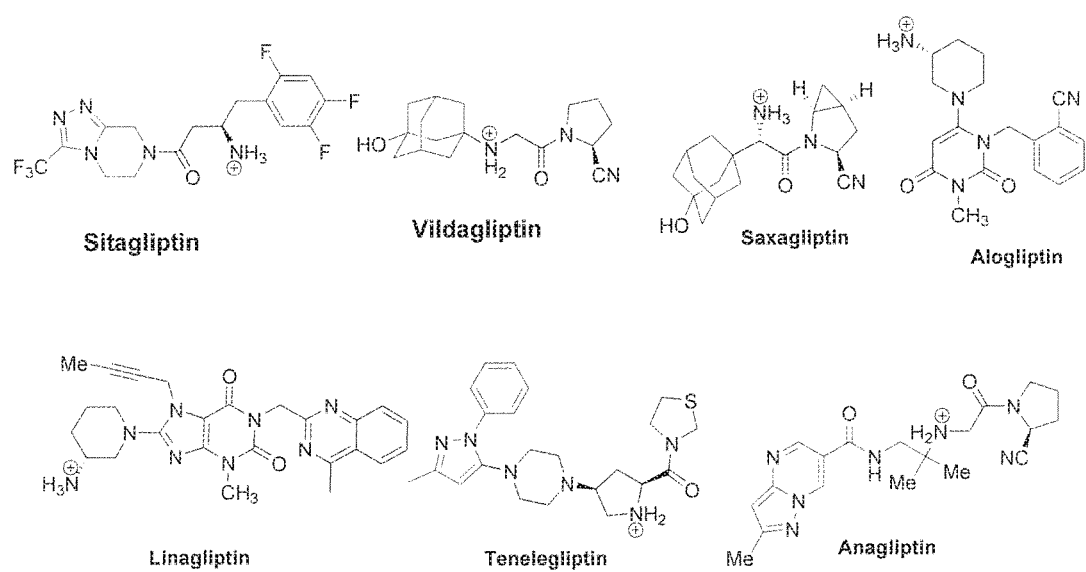
FIG. 1. Structural features of DPP-4 inhibitors and some examples of marketed drugs.
Figure 2A:
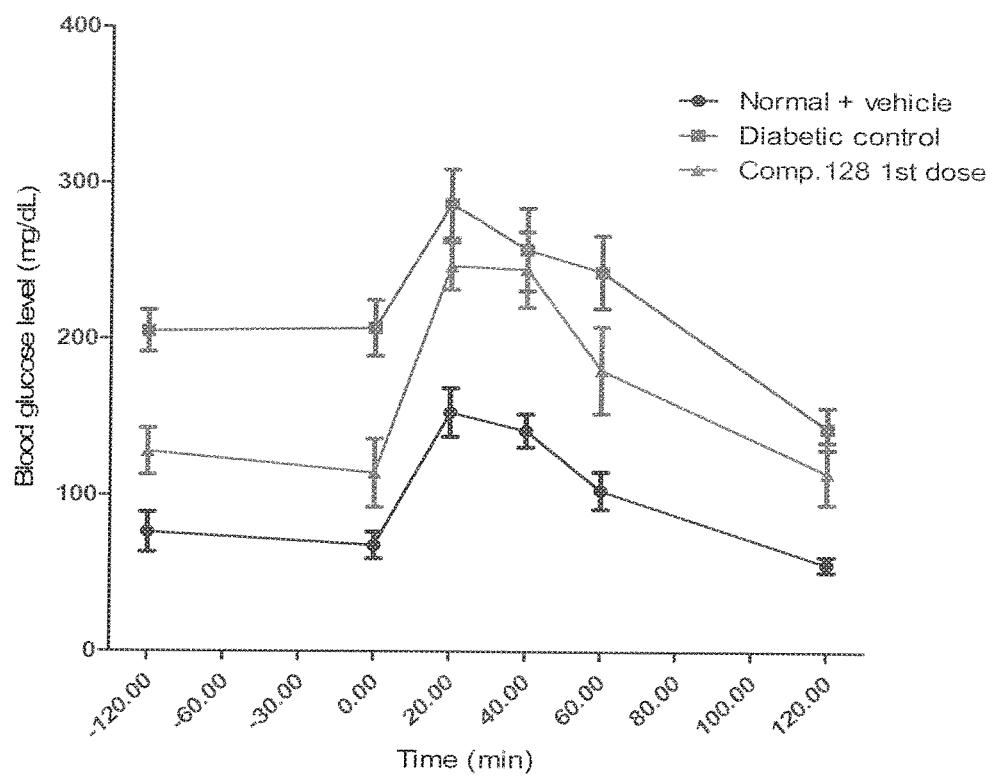
FIG. 2A-D. Blood glucose level (0-120 min) after oral glucose loading in 14 hr fasted diabetic mice, 2 hr pretreatment with a single oral dose of compound No. 128 (A), 129 (B), 130 (C) and 131 (D).
Figure 2B:
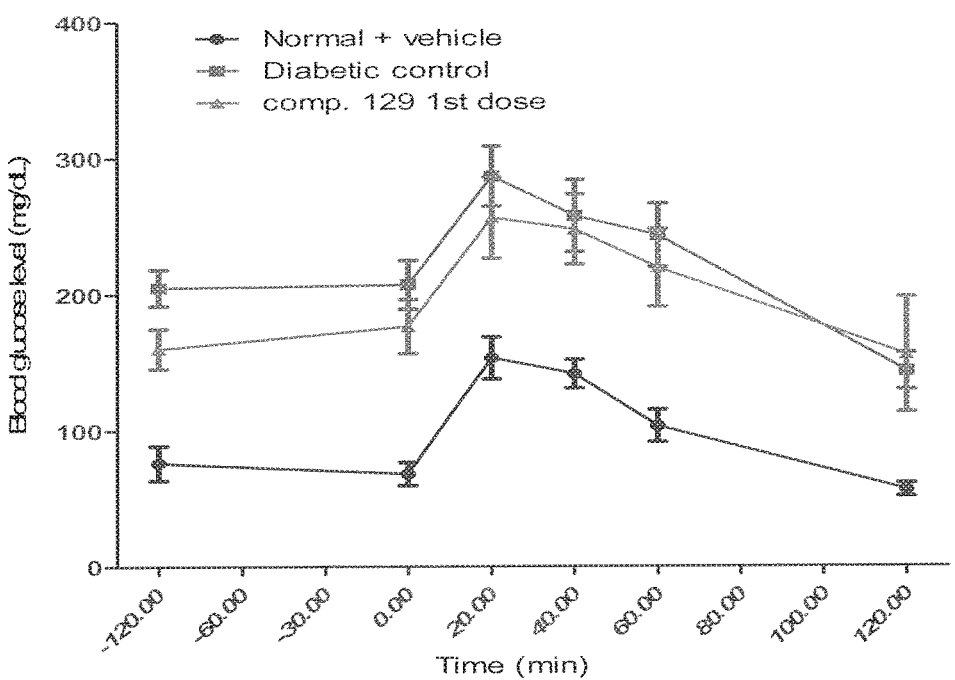
Figure 2C:
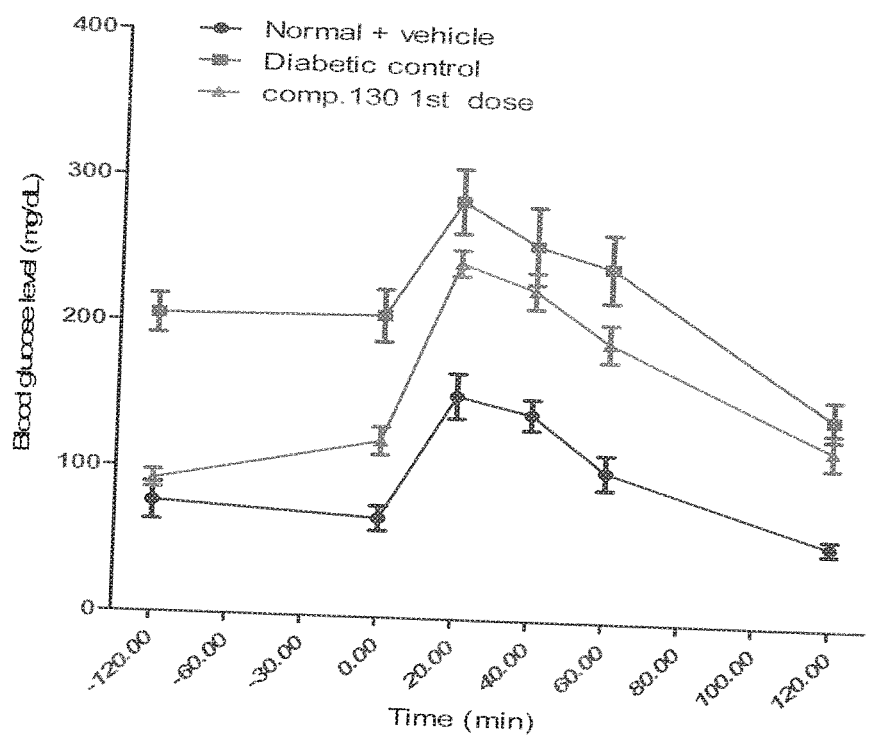
Figure 2D:
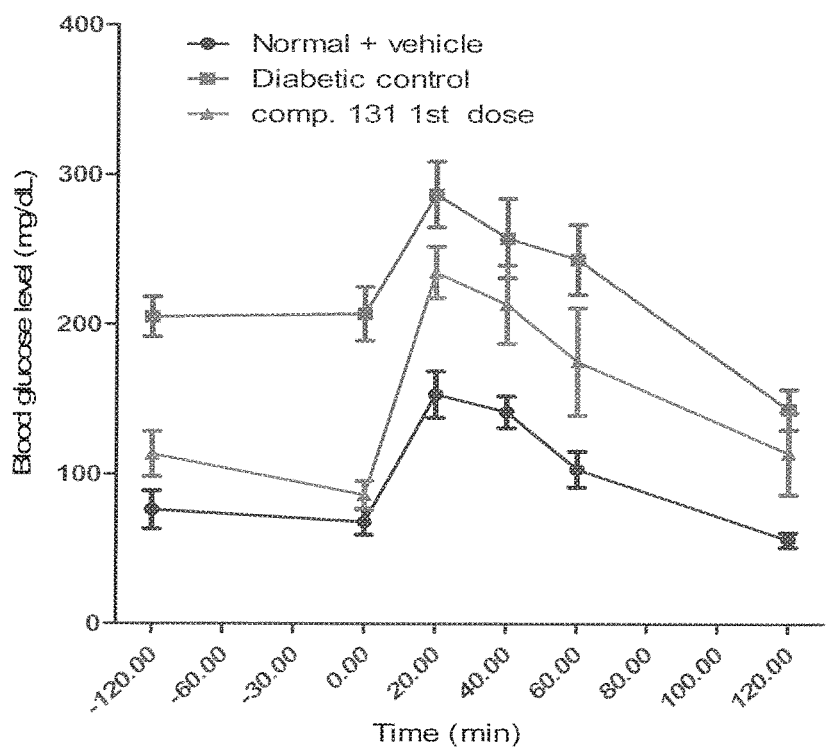
Figure 3:
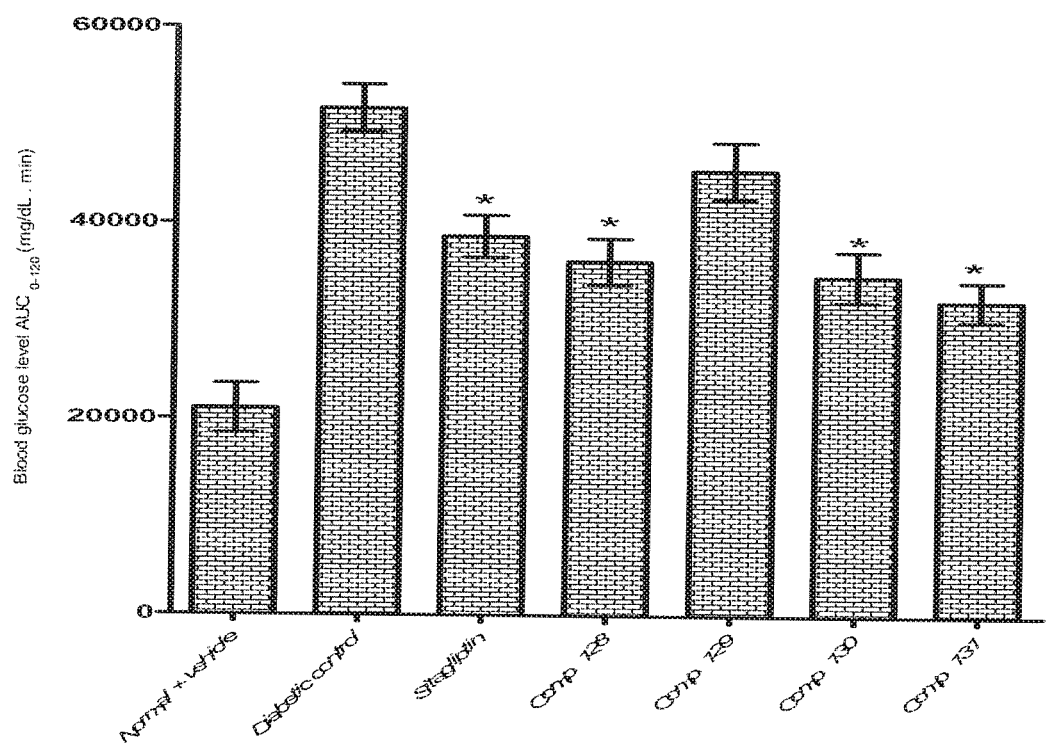
FIG. 3. Area under the curve (AUC) graph for 0-120 minutes after oral glucose loading during oral glucose tolerance test in 14 hr fasted diabetic mice, 2 hr pretreatment with a single oral dose of compounds Nos. 128, 129, 130 and 131. * indicates a significant difference compared to diabetic control, P<0.05.
Figure 4A:
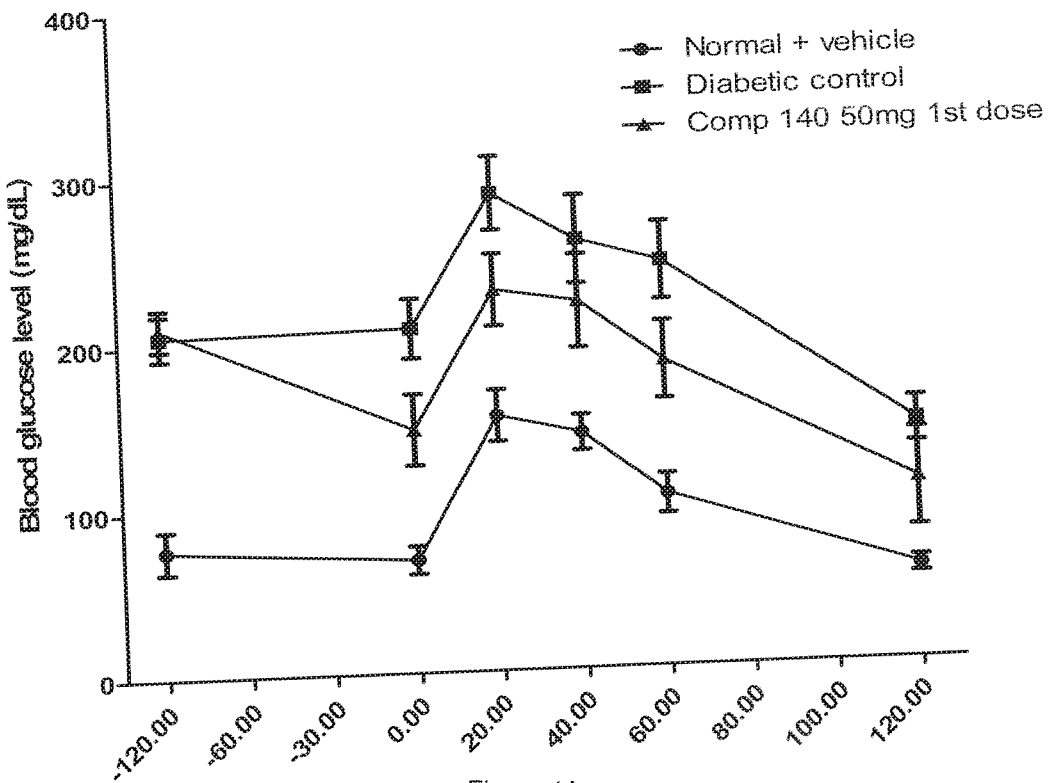
FIGS. 4A and B. Blood glucose level (0-120 min) after oral glucose loading in 14 hr fasted diabetic mice, 2 hr pretreatment with a single oral dose of compound No. 140 (A) and 142 (B).
Figure 4B:
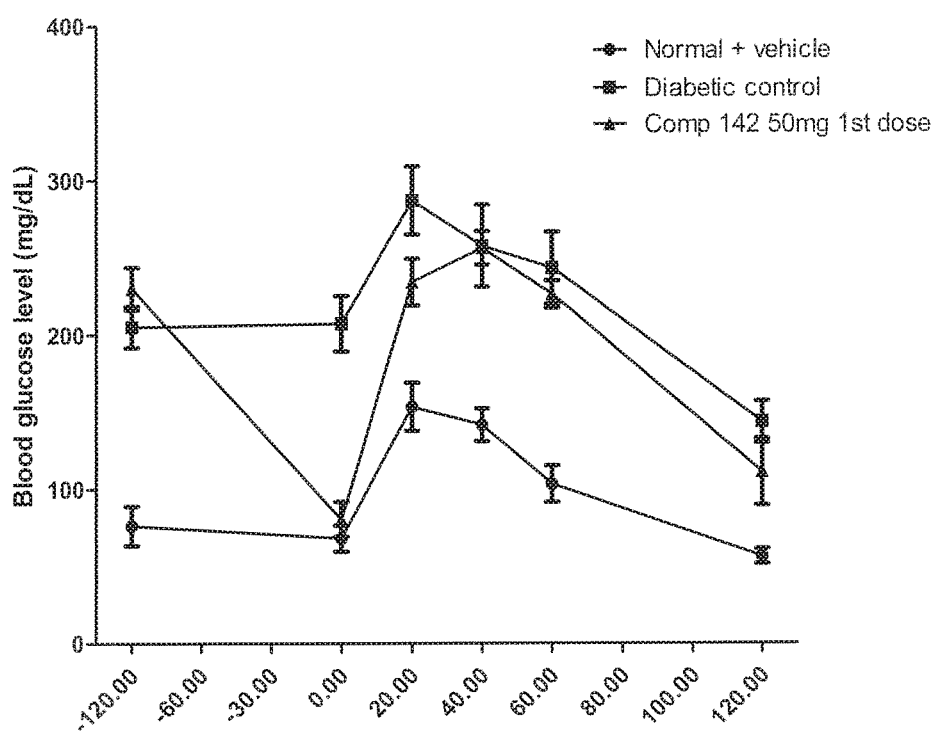
Figure 5:
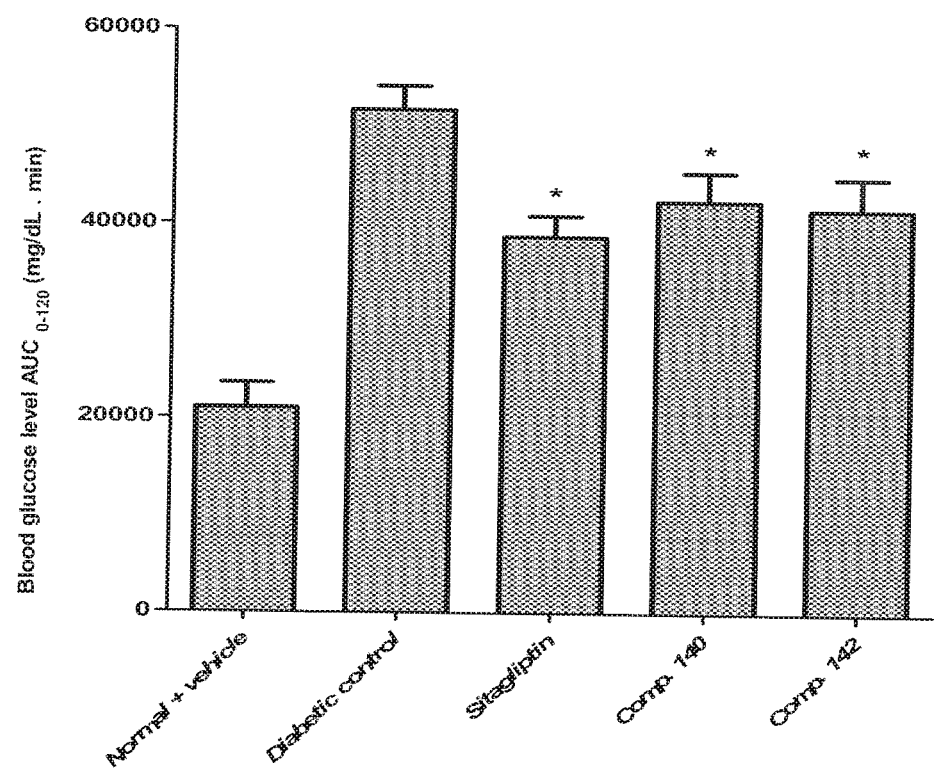
FIG. 5. Area under the curve (AUC) graph for 0-120 minutes after oral glucose loading during oral glucose tolerance test in 14 hr fasted diabetic mice, 2 hr pretreatment with a single oral dose of compounds Nos. 140 and 142, with a dose of 50 mg/kg. * indicates a significant difference compared to diabetic control, P<0.05.
Figure 6A:
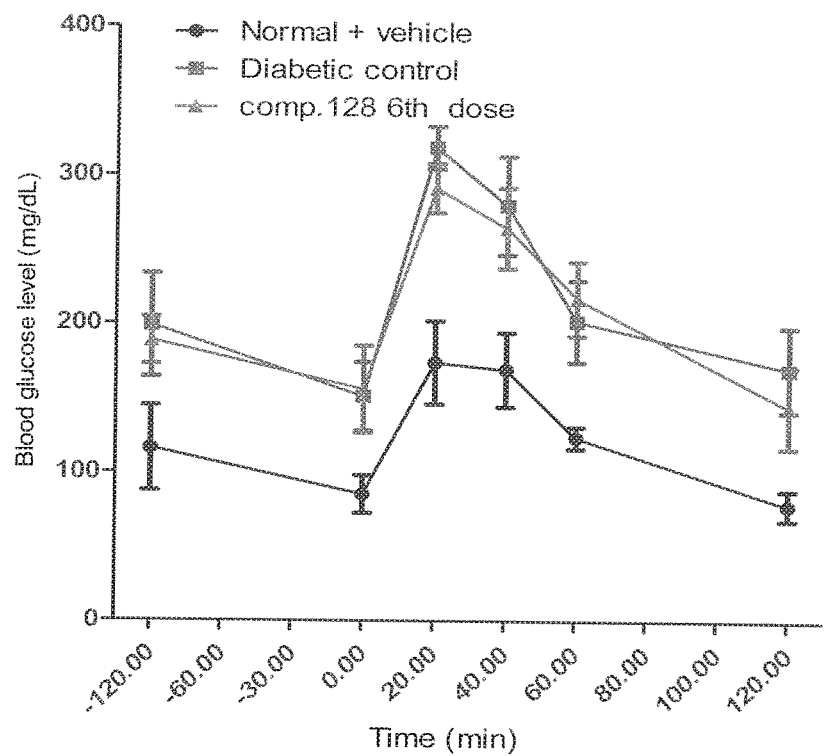
FIG. 6A-C. Blood glucose level (0-120 min) after oral glucose loading in 14 hr fasted diabetic mice, 2 hr pretreatment for 6 says with compound No. 128 (A), 129 (B) and 130 (C).
Figure 6B:
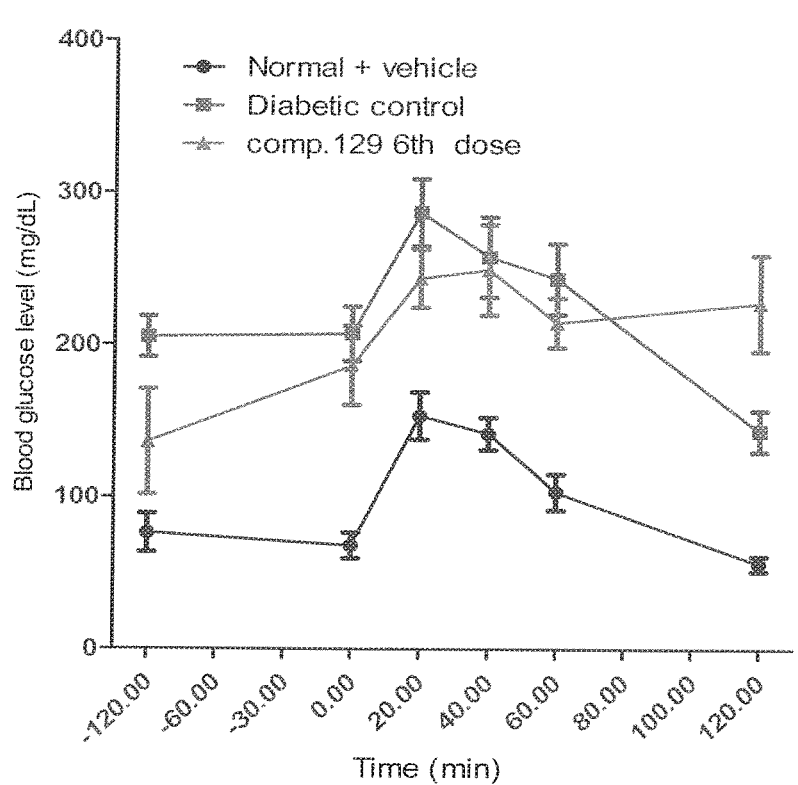
Figure 6C:
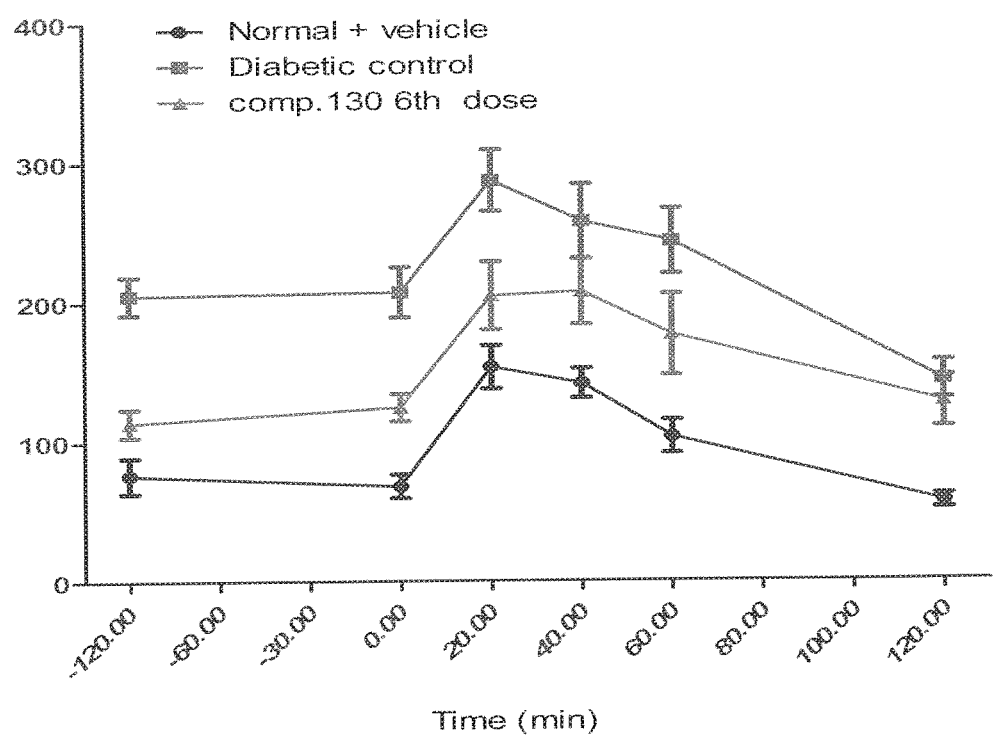
Figure 7A:
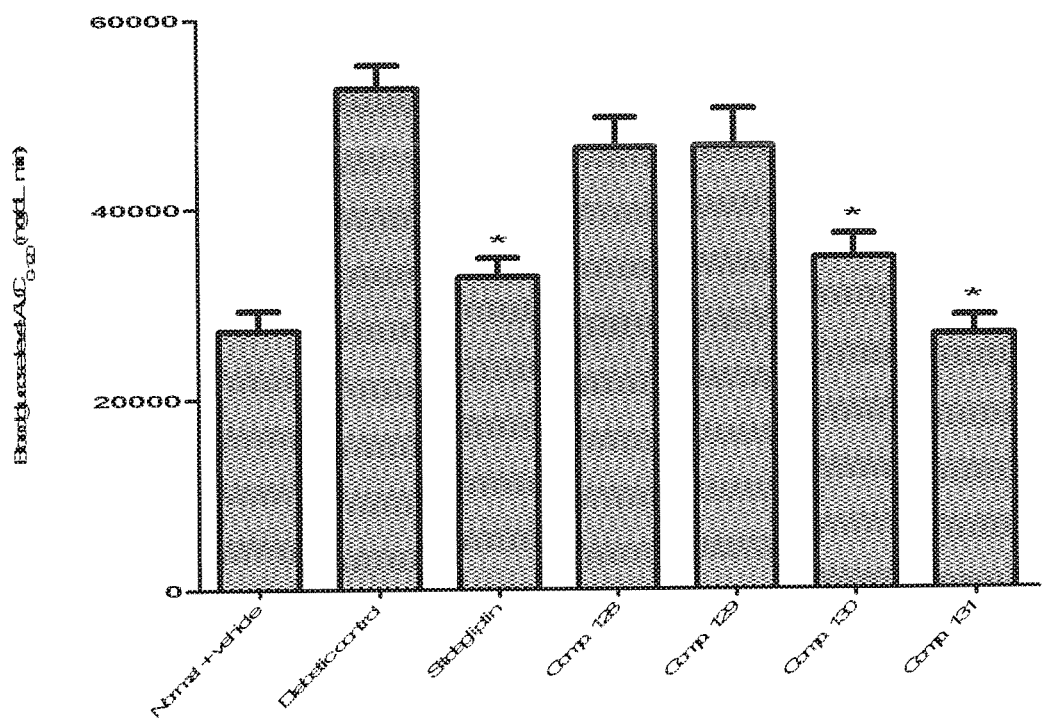
FIGS. 7A and B. Area under the curve (AUC) graph for 0-120 minutes after oral glucose loading during oral glucose tolerance test in 14 hr overnight fasted diabetic mice, 2 hr pretreatment with six oral doses of compounds Nos. 128, 129, 130 and 131 (A), and compounds 140 and 142 (B), with doses of 50 mg/kg. * indicates a significant difference compared to diabetic control, P<0.05.
Figure 7B:
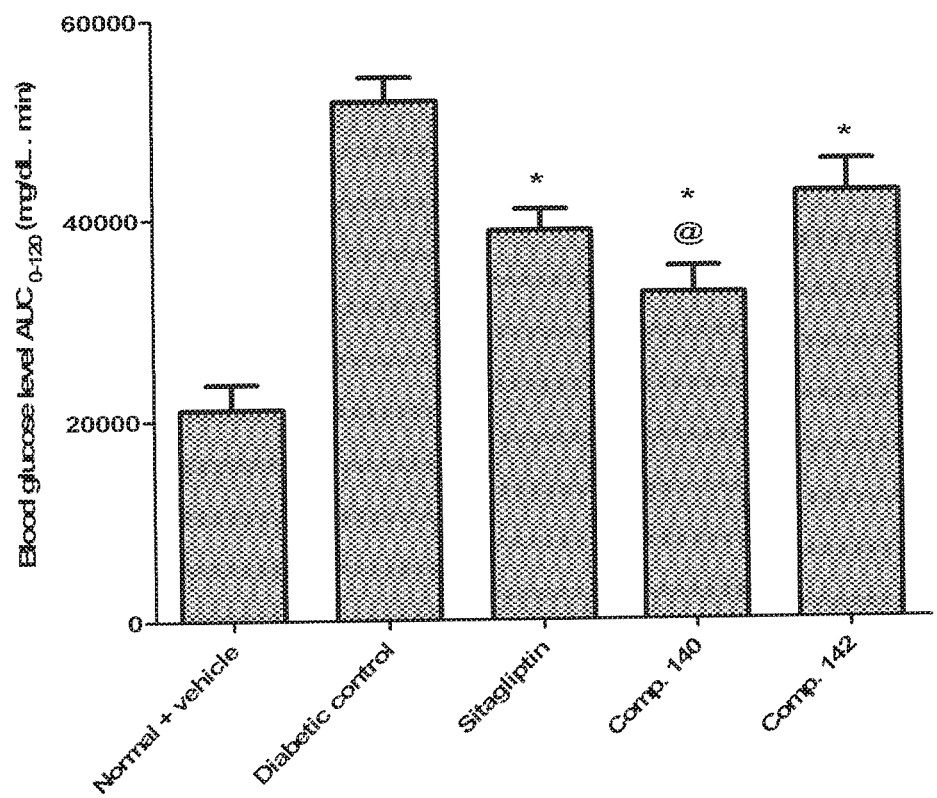
Figure 8A:
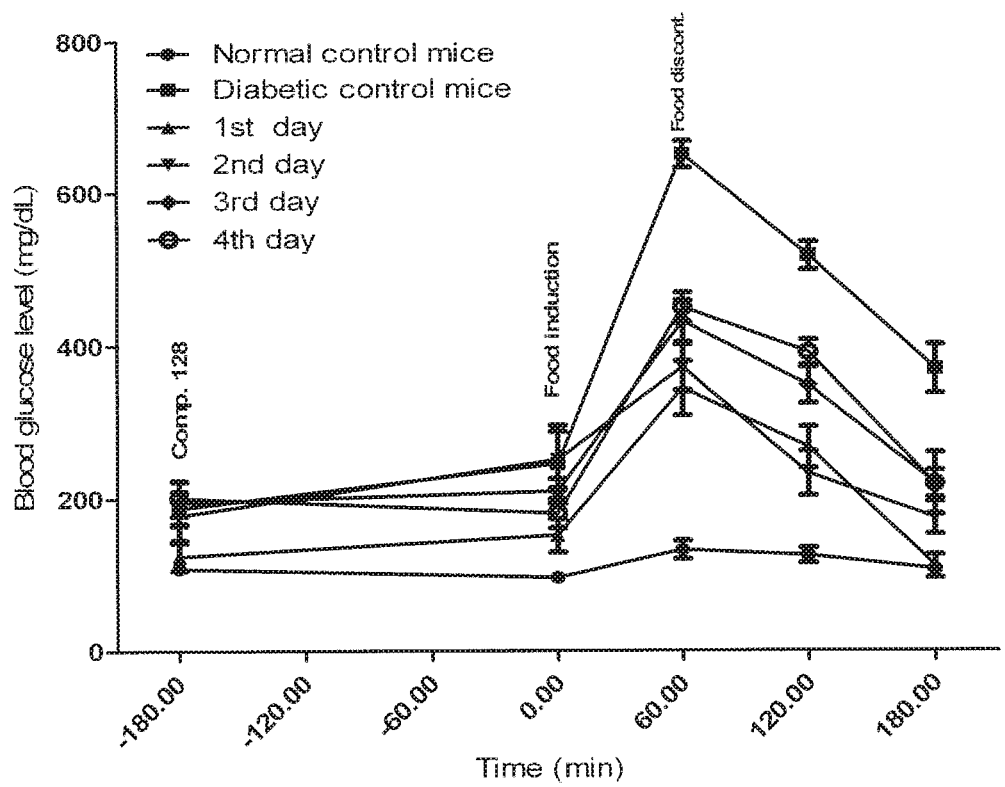
FIGS. 8A and B. Tests of Compound 128 (50 mg/kg) in overnight (14 hr) fasted diabetic mice. A, effect on blood glucose levels during meal feeding (1 hr) and 2 hrs after meal discontinuation during 4 days of treatment; B, blood glucose AUC 0-180 min postmeal feeding 3 hr pretreated. @ indicates a significant difference compared to diabetic control, P<0.05.
Figure 8B:
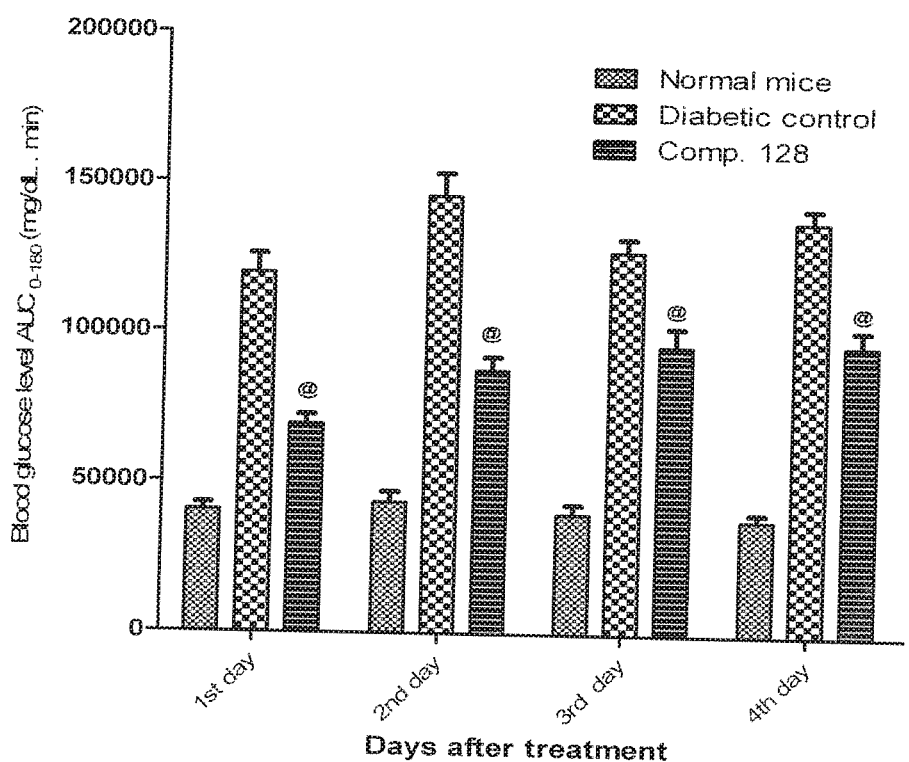
Figure 9A:
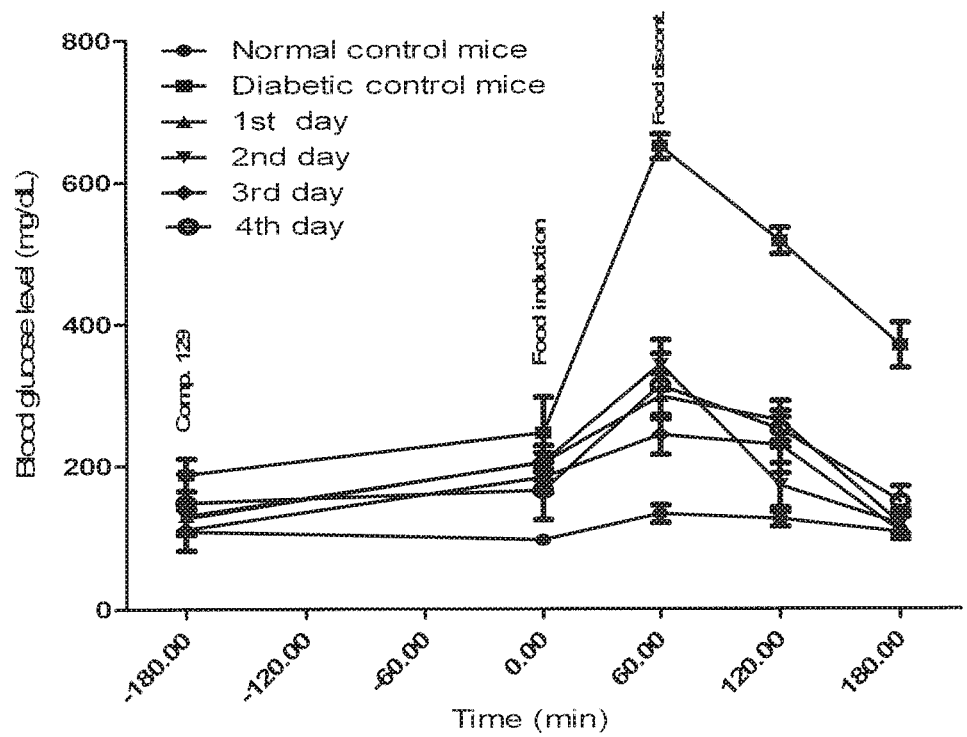
FIGS. 9A and B. Tests of Compound 129 (50 mg/kg) in overnight (14 hr) fasted diabetic mice. A, effect on blood glucose levels during meal feeding (1 hr) and 2 hrs after meal discontinuation during 4 days of treatment; B, blood glucose AUC 0-180 min postmeal feeding 3 hr pretreated. @ indicates a significant difference compared to diabetic control, P<0.05.
Figure 9B:
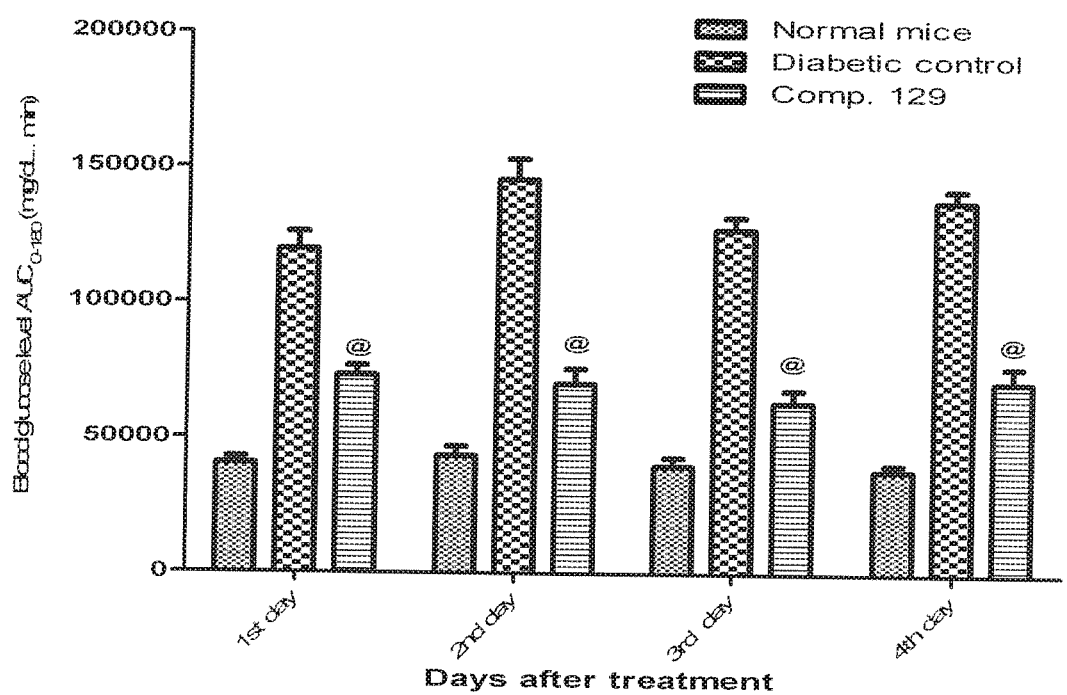
Figure 10A:
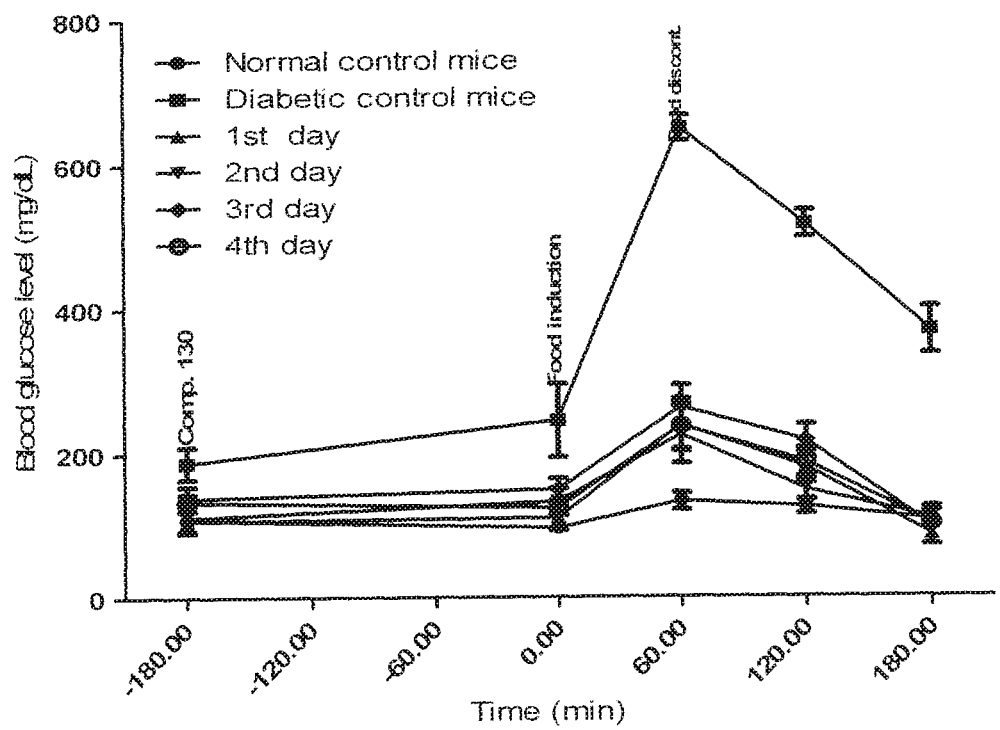
FIGS. 10A and B. Tests of Compound 130 (50 mg/kg) in overnight (14 hr) fasted diabetic mice. A, effect on blood glucose levels during meal feeding (1 hr) and 2 hrs after meal discontinuation during 4 days of treatment; B, blood glucose AUC 0-180 min postmeal feeding 3 hr pretreated. @ indicates a significant difference compared to diabetic control, P<0.05.
Figure 10B:
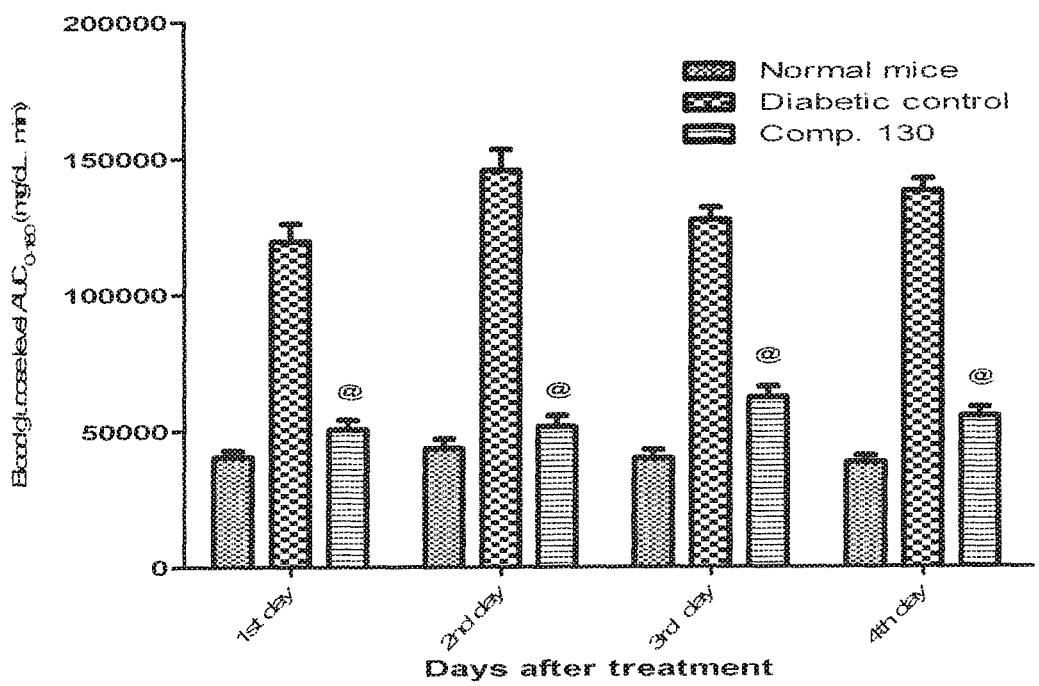
Figure 11A:
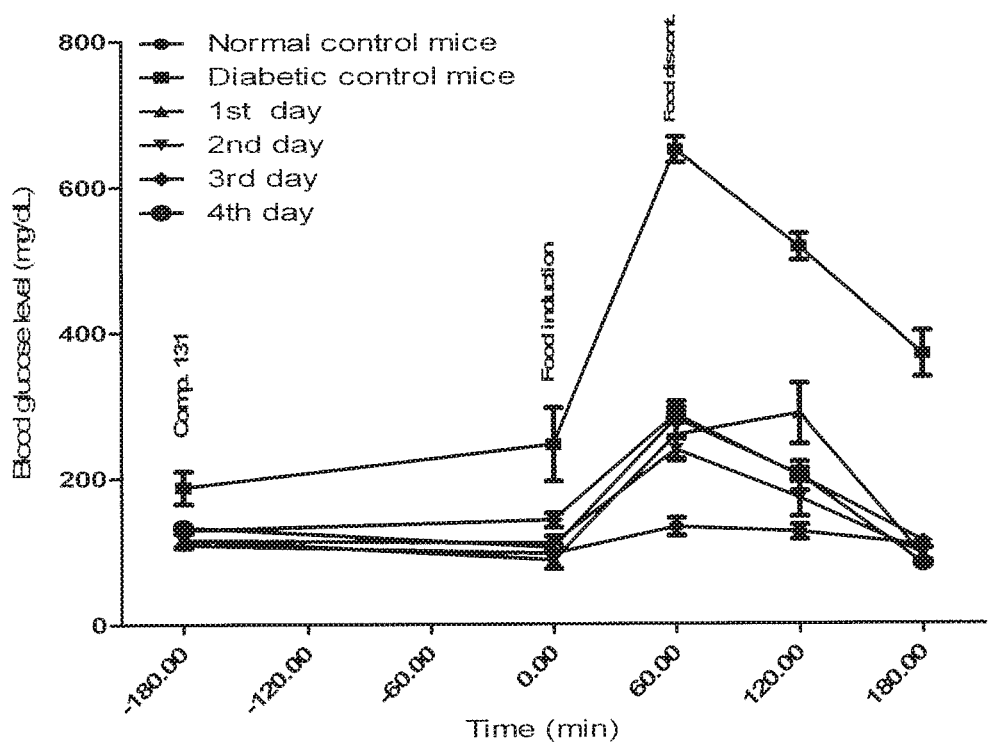
FIGS. 11A and B. Tests of Compound 131 (50 mg/kg) in overnight (14 hr) fasted diabetic mice. A, effect on blood glucose levels during meal feeding (1 hr) and 2 hrs after meal discontinuation during 4 days of treatment; B, blood glucose AUC 0-180 min postmeal feeding 3 hr pretreated. @ indicates a significant difference compared to diabetic control, P<0.05.
Figure 11B:
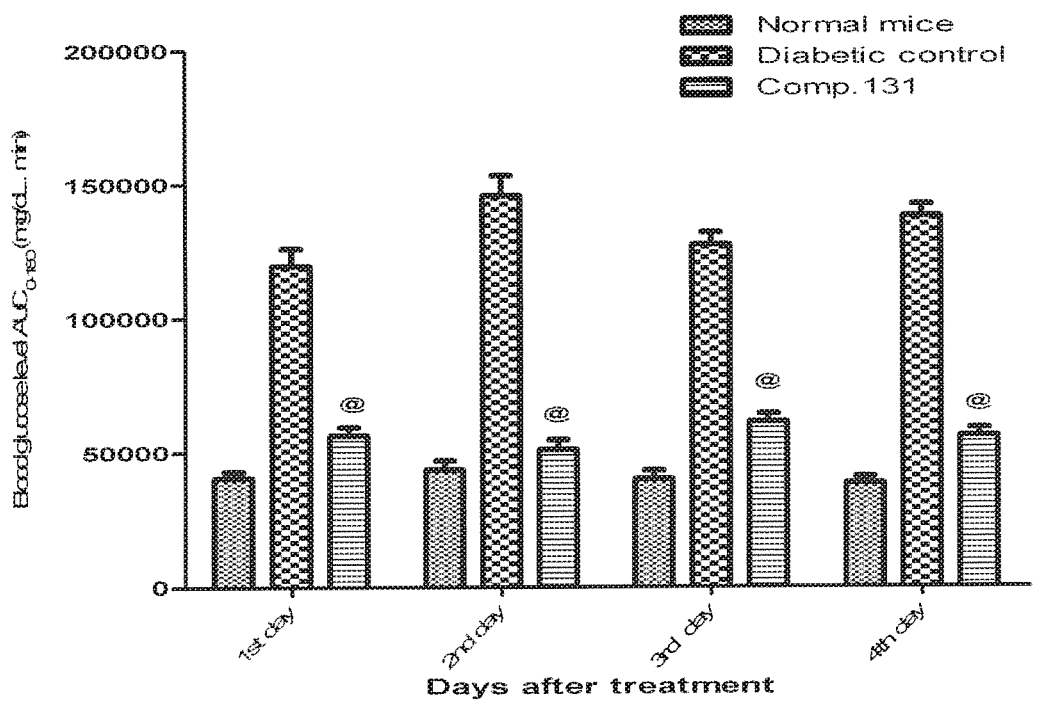
Figure 12A:
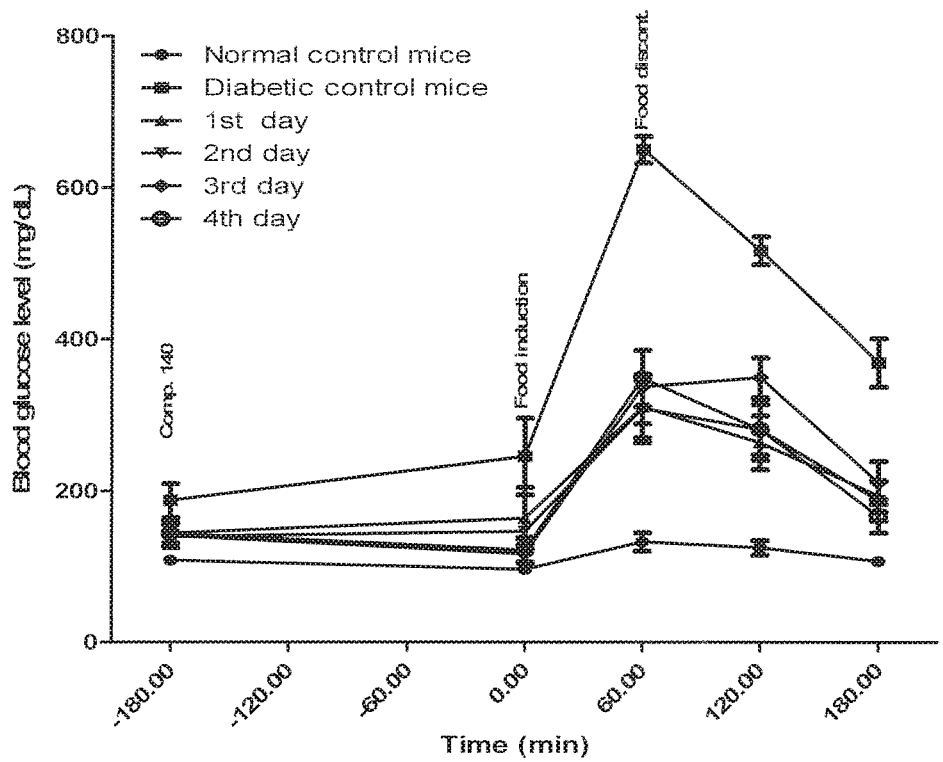
FIGS. 12A and B. Tests of Compound 140 (50 mg/kg) in overnight (14 hr) fasted diabetic mice. A, effect on blood glucose levels during meal feeding (1 hr) and 2 hrs after meal discontinuation during 4 days of treatment; B, blood glucose AUC 0-180 min postmeal feeding 3 hr pretreated. @ indicates a significant difference compared to diabetic control, $P<0.05$.
Figure 12B:
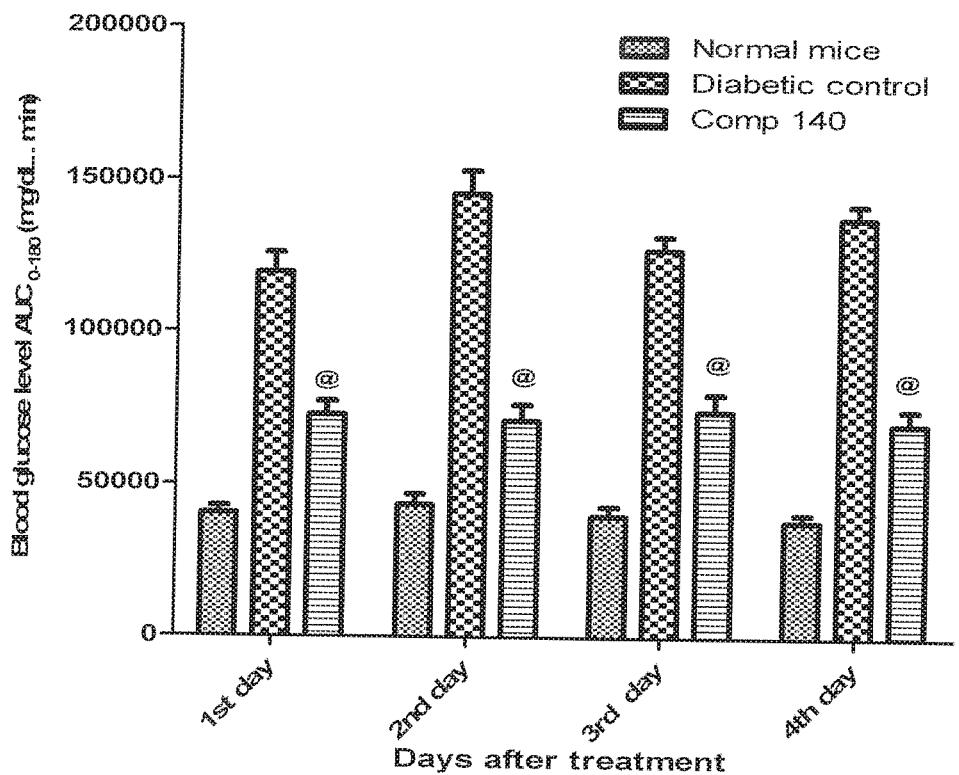

The approach taken herein to develop new DPP-4 inhibitors involved merging the structures of sitagliptin (3-(trifluoromethyl)-5,6,7,8-tetrahydro-[1,2,4]triazolo[4,3-a]pyrazine) and vildagliptin, both of which are depicted below, and saxagliptin (see FIG. 1). Certain aspects of the new compounds are represented by the generic structure denominated "non-basic analogues".

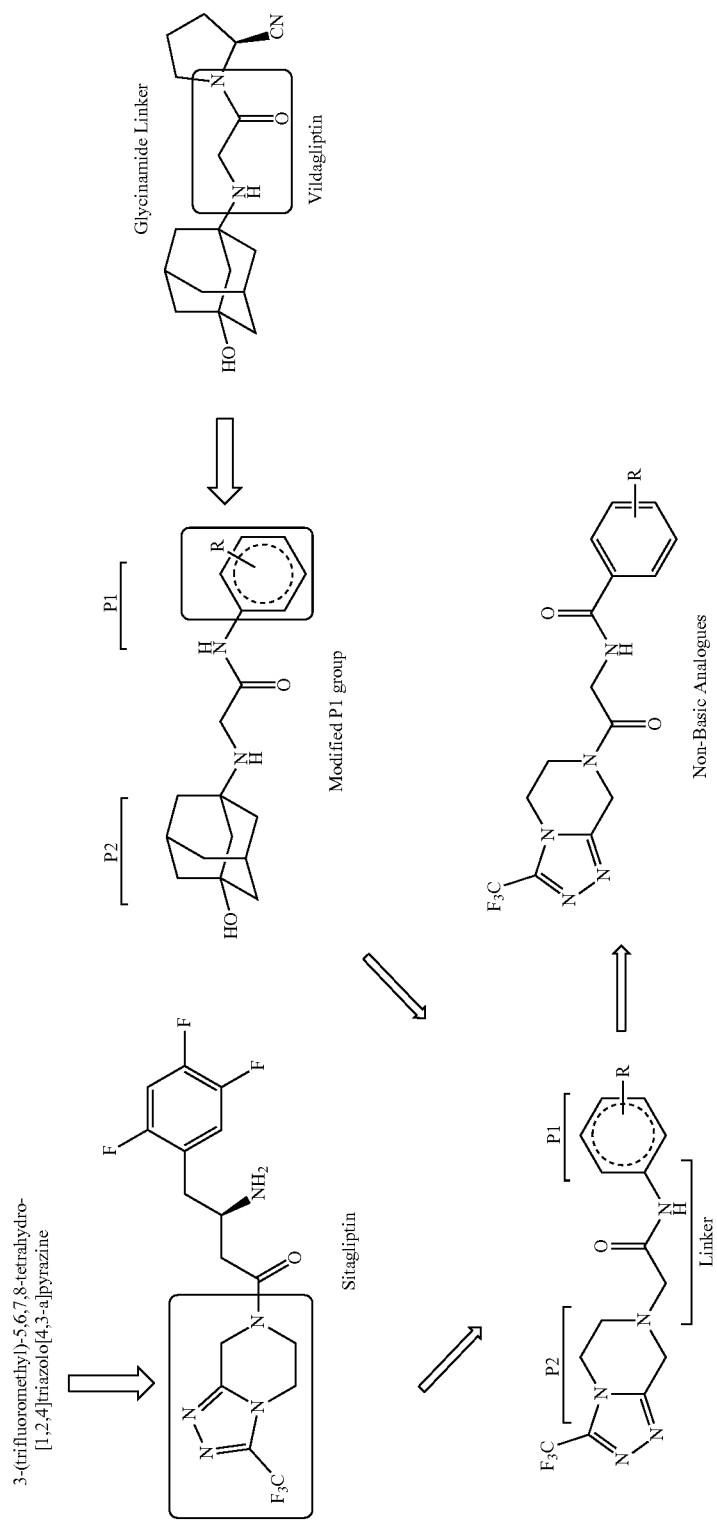

In some aspects, the DPP-4 inhibitors described herein have a generic structure as depicted in Formula I:

Formula I

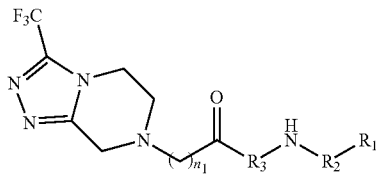

$n_1$=0-2;
R1=i) an alicyclic group such as a saturated or unsaturated monocyclic aliphatic ring, alone or fused with cyclopropane or cyclobutene, which may be unsubstituted or substituted by replacement of a carbon atom of the ring with a heteroatom; and optionally including one or more substituents attached to the ring; or
ii) a substituted or unsubstituted aromatic group such as a monocyclic aromatic ring, optionally including one or more substituents attached to the ring;
R2=present or absent and if present is C=O; $(CH_2)_n$ where n=1-4 (if R2 is present, n=1=4; n=0 is R2 is absent), S, SO, $SO_2$, NR (where R=H, $CH_3$, $CH_2CH_3$, or $NH(CH_2)_n$ where n=0-4; and
R3 is present or absent and if present is $(CH_2)_n$ where n=1-4, (if R3 is present, n=1=4; n=0 is R3 is absent), S, SO, $SO_2$, NR (where R=H, $CH_3$, $CH_2CH_3$, or $NH(CH_2)n$ where n=0-4;
and salts and isomers thereof, e.g. stereoisomers such as R and S enantiomers.

"0-2" can be 0, 1, or 2 and "0-4" can be 0, 1, 2, 3, or 4.

As used herein, a "substituted" ring is a ring comprising a heteroatom within the ring, whereas a functional group attached to an atom of the ring if referred to as a substituent.

Examples of substituted or unsubstituted, saturated or unsaturated monocyclic aliphatic rings include but are not limited to: cyclobutane, cyclopentane, cyclohexane and cycloheptane; examples of substituted (heterocyclic) forms of cyclobutane, cyclopentane, cyclohexane and cycloheptane include those forms in which one or more C atoms of the ring is replaced by, for example, O, N, or S. If saturated and one double bond is present, then the group is referred to as e.g. cyclobutene, cyclopentene, cyclohexene and cycloheptene.

The monocyclic aliphatic groups and/or the aromatic groups may also comprise one or more substituents (chemical functional groups) that are attached to the ring, such as CN, OH, =O, $CH_3$, $CH_2CH_3$, isopropyl, cyclopropyl, $SO_2CH_3$, $SO_2NH_2$, $NH(CH_3)$, $N(CH_3)_2$, $NHCOCH_3$.

In some aspects, R1 is cyclohexane.

Exemplary monocyclic aromatic rings include but are not limited to: phenyl, pyridyl, pyrrole, imidazole, thiazole, furan, oxazole, pyrimidine, 1,2,4-triazine, 1,3,5-triazine, pyrazine, pyrazole, isoxazole, isothiazole, 1,3,4-oxadiazole, 1,3,4-thiadiazole, etc. and forms of those groups which also include one or more substituents attached to an atom of the ring.

In some aspects, R1 is

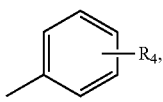

where R4 may be present or absent and when present, is CN, halogen (e.g. F, Cl), $OCH_3$, OH, $NO_2$, $CH_3$, $NH_2$, $NHCH_3$, $N(CH_3)_2$, $CH_3$, $CHF_2$, $CH_2F$, etc. The one or more substituents can be present at the ortho, meta or para positions of the ring.

Exemplary compounds disclosed herein include but are not limited those depicted below, where numbering of compounds is the same as that used in the biological data graphs presented herein.

GLP-128

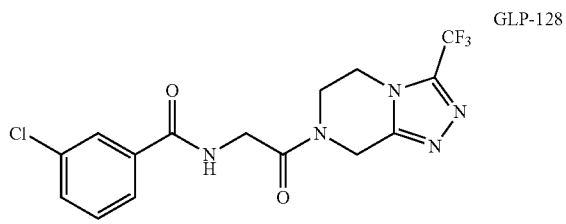

GLP-129

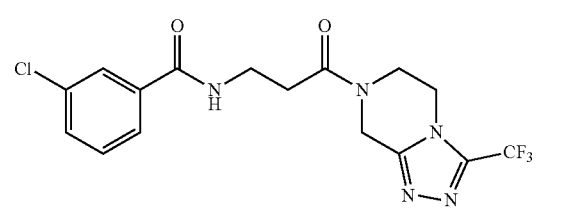

GLP-30

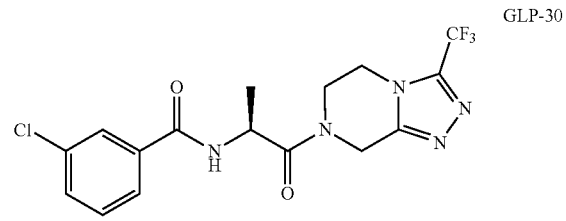

GLP-131

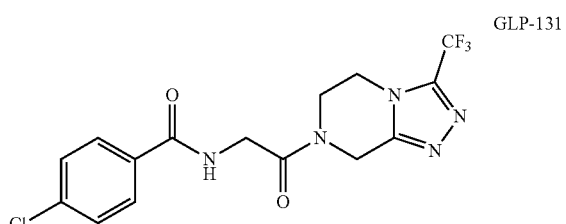

GLP-136

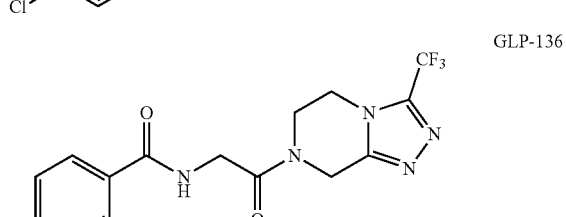

GLP-138

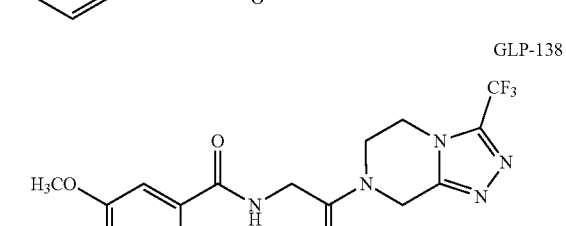

-continued

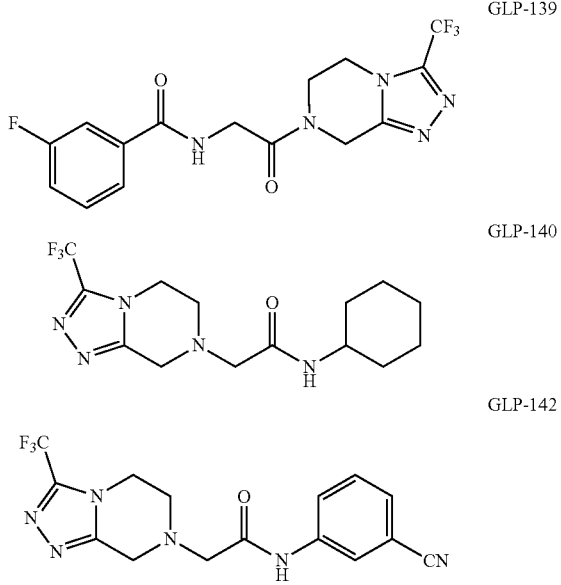

GLP-139

GLP-140

GLP-142

Compositions and Administration

The compounds described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations and compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to: ion exchangers, alumina, aluminum stearate, lecithin, serum proteins (such as human serum albumin), buffer substances (such as Tween® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compounds may be administered in vivo by any suitable route including but not limited to: by injection (e.g. intravenous, intraperitoneal, intramuscular, subcutaneous, and the like), by absorption through epithelial or mucocutaneous linings (e.g., nasal, oral, gastrointestinal mucosa, and the like); or, orally (e.g. as a pill, capsule, liquid, etc.). In preferred embodiments, the mode of administration is oral.

In addition, the compositions may be administered in conjunction with other treatment modalities such as other drugs used to treat hyperglycemia and/or diabetes, e.g. a sulphonylurea, a thiazolidinedione, metformin, and/or insulin. The compositions may be administered with a separate composition of one or more other drugs (especially for insulin, which is typically injected); or the one or more other drugs may be combined together with one or more of the present compounds in a single preparation, e.g. in a tablet that includes a compound as described herein and one or more of e.g. a sulphonylurea, a thiazolidinedione and metformin.

Methods of Treatment

The invention also encompasses methods of using the compounds to treat hyperglycemia (high blood sugar, high blood glucose) and diseases and conditions associated with high blood sugar, such as pre-diabetes, diabetes, hyperosmolar hyperglycemic nonketotic syndrome (HHNS), etc. "Hyperglycemia" may refer to fasting hyperglycemia, defined as a blood glucose level above 130 mg/dL after at least 8 hours of fasting; and/or postprandial or reactive hyperglycemia defined as a blood glucose level above 180 mg/dL 1-2 hours after eating. The type of diabetes that is treated may be Type I or Type II, and is usually Type II. The treatment methods include a step of administering to a subject in need thereof a therapeutically effective amount of at least one compound disclosed herein. Administration of the compounds is therapeutically effective to treat or prevent at least one symptom of hyperglycemia and related or associated diseases, such as but not limited to: frequent urination, increased thirst, blurred vision, fatigue, headache; the buildup of toxic acids (ketones) in blood and urine (ketoacidosis), signs and symptoms of which include: fruity-smelling breath, nausea and vomiting, shortness of breath, dry mouth, weakness, confusion, coma, and abdominal pain.

In some aspects, administration of the compounds completely prevents or reverses one or more symptoms of hyperglycemia and related or associated diseases and conditions. However, those of skill in the art will recognize that much benefit can accrue to a subject even if a complete cure or control of a disease or symptoms thereof does not take place Lowering or lessening, or decreasing the frequency of, or slowing the onset of one of more symptoms may also be of great benefit.

The amount of a compound of the invention may vary from subject to subject and from time period to time period for a given subject, depending on e.g. the weight, age, genetic background, overall health, etc. as well as the tendency of the subject to adopt life-style changes such as undertaking exercise and/or adopting healthy eating programs, which may decrease or eliminate the need for medication. Alternatively, a subject may develop a need for a higher dose over time, or may require a lower dose when the compound is administered with another anti-hypergylcemia drug. Generally, a single dose of a compound is in the range of from about 20 to about 500 mg per day, (e.g. about 20, 30, 40, 50, 60, 70, 80, 90, 100, 150, 200, 250, 300, 350, 400, 450 or 500 mg per dose), and preferably is about 50 mg per dose, taken once or twice a day, so that a total dose per day could be e.g. 50 (one per day) or 100 mg (50 mg twice per day).

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Type 2 Diabetes Mellitus (T2DM) is wide-spread non-infectious chronic illness that can be controlled by increasing endogenous substances called gliptins. Gliptins are destroyed by the enzyme dipeptidyl peptidase (DPP-4), a serine protease that excises the first two terminal amino acids of gliptins. This Example describes the utilization of some structural features of vildagliptin, saxagliptin and sitagliptin, antidiabetic drugs which are DPP-4 inhibitors, to design novel compounds that possess antidiabetic activity in animal models of induced high glucose levels and with induced diabetes. Selected compounds demonstrated strong inhibition of DPP-4, the major target of gliptin antidiabetic agents.

A. Chemical Synthesis

Compounds were synthesized according to standard literature procedure described in scheme 1. All compounds were confirmed with different techniques such as $^1$H NMR, $^{13}$C NMR, FT-IR and LC/MS.

Scheme 1. Synthesis of di-amide derivatives GLP-128, 129, 130, 131, 136, 138, 139.

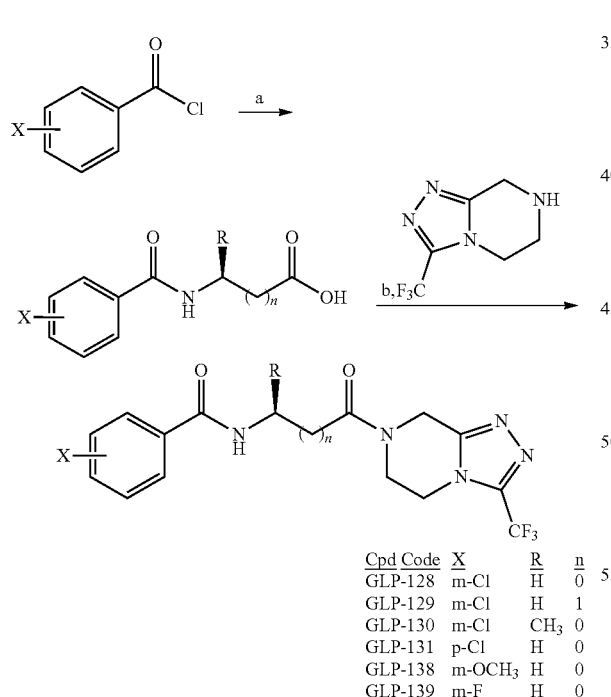

| Cpd Code | X | R | n |
|---|---|---|---|
| GLP-128 | m-Cl | H | 0 |
| GLP-129 | m-Cl | H | 1 |
| GLP-130 | m-Cl | CH$_3$ | 0 |
| GLP-131 | p-Cl | H | 0 |
| GLP-138 | m-OCH$_3$ | H | 0 |
| GLP-139 | m-F | H | 0 |

Reagents and Conditions: a) Et$_3$N, DCM, 0° C. to r.t., 2 h: b) ClCO$_2$Et, Et$_3$N, DCM, 0° C. to r.t., 2 h $^1$H NMR of GLP128: DMSO, δ 3.94-3.4.23 (m, br, 6H, 3CH$_2$), 4.92 (s, 1H, CH$_2$), 7.24-7.27 (t, 1H, Arom-H), 7.34-7.35 (d, 1H, Arom-H), 7.62-7.63 (d, 1H, Arom-H), 7.7 (br, s, 1H, Arom-H), 7.84-7.95 (br, m, 1H, NH).

$^1$H NMR of GLP129: DMSO, δ 2.66 (br, s, 2H, CH$_2$), 3.48-3.50 (br, t, 2H, CH$_2$), 3.82-3.889 (d, 2H, CH$_2$), 3.95-4.02 (d, 2H, CH$_2$), 4.78-4.81 (d, 2H, CH$_2$), 7.12-7.18 (m, 1H, Arom-H), 7.23 (br, 2H, Arom-H), 7.47-7.51 (dd, 1H, Arom-H), 7.57-7.59 (d, 1H, Arom-H), 7.78 (br, t, 1H, NH).

$^1$H NMR of GLP130: DMSO, δ 1.47-1.48 (d, 3H, CH$_3$), 3.97-3.99 (t, 2H, CH$_2$), 4.17-4.19 (t, 2H, CH$_2$), 4.94 (s, 2H, CH$_2$), 5.17-5.21 (q, 1H, CH), 7.35-7.38 (t, 1H, Arom-H), 7.46-7.51 (m, 2H, Arom-H), 7.67-7.69 (m, br, 1H, Arom-H), 7.67-7.70 (m, 1H, Arom-H), 7.82-7.83 (br, t, 1H, NH).

$^1$H NMR of GLP131: DMSO, δ 3.55-3.56 (d, 2H, CH$_2$), 3.88-3.90 (d, 2H, CH$_2$), 4.08-4.09 (d, 2H, CH$_2$), 4.87 (s, 2H, CH$_2$), 7.02-7.04 (m, 2H, Arom-H), 7.84-7.86 (br, 1H, NH). 7.95-7.97 (m, 2H, Arom-H).

$^1$H NMR of GLP136: DMSO, δ 3.55-3.56 (d, 2H, CH$_2$), 3.88-3.90 (d, 2H, CH$_2$), 4.08-4.09 (d, 2H, CH$_2$), 4.87 (s, 2H, CH$_2$), 7.19-7.24 (m, 2H, Arom-H), 7.23-7.29 (m, 3H, Arom-H), 7.28-7.30 (br, m, 1H, NH).

$^1$H NMR of GLP138: DMSO, δ 3.78 (a, 3H, OXH$_3$), 3.89-3.91 (t, br, 2H, CH$_2$), 4.11-4.13 (t, 2H, CH$_2$), 4.36 (s, 1H, CH$_2$), 6.97-7.00 (m, 1H, Arom-H), 7.05-7.06 (dd, 1H, Arom-H), 7.27-7.29 (t, 1H, Arom-H), 7.31-7.33 (t, 1H, Arom-H), 7.43-7.44 (br, t, 1H, NH).

$^1$H NMR of GLP139: DMSO, 3.88-3.89 (t, 2H, CH$_2$), 4.08-4.10 (t, 2H, CH$_2$), 4.12-4.14 (t, 2H, CH$_2$), 4.85 (br, s, 2H, CH$_2$), 7.10-7.13 (m, 1H, Arom-H), 7.20 (br, s, 1H, Arom-H), 7.30-7.34 (m, 1H, Arom-H), 7.44-7.46 (m, 1H, Arom-H), 7.49-7.50 (br, t, 1H, NH). N.B. All compounds were confirmed with LC/MS and showed excellent purities (over 95%).

Scheme 2. Synthesis of mono-amide derivatives GLP-140, 142.

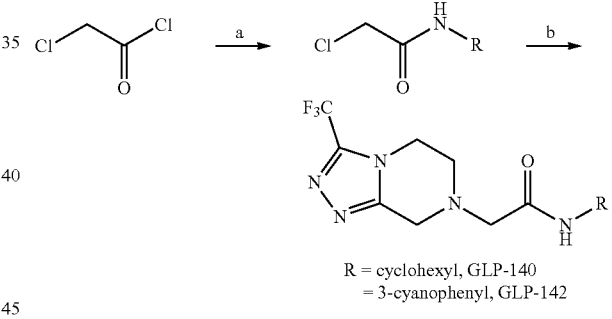

R = cyclohexyl, GLP-140
= 3-cyanophenyl, GLP-142

Reagents and Conditions: a) Amine RNH$_2$, Et$_3$N, DCM, −20° C., 30 min then r.t. 2 h: b) 3-(trifluoromethyl)-5,6,7,8-tetrahydro-[1,2,4]triazolo[4,3-a]pyrazine, K$_2$CO$_3$, DMF, heat, 3 h.

$^1$H NMR of GLP140: DMSO, 1.23 (br, 6H, 3CH$_2$), 1.66-1.71 (t, 4H, 2 CH$_2$), 2.4 (br, m, 1H, CH), 2.98-3.00 (t, 2H, CH$_2$), 3.23 (s, 2H, CH$_2$) 3.95 (s, 2H, CH$_2$), 4.17-4.19 (t, 2H, CH$_2$), 7.73-7.74 (br, d, 1H, NH).

$^1$H NMR of GLP142: DMSO, 3.11-3.13 (t, 2H, CH$_2$), 3.47 (s, 2H, CH$_2$), 3.98 (s, 2H, CH$_2$), 4.22 (t, 2H, CH$_2$), 7.53 (br, m, 2H, Arom-H), 7.7.90 (d, 1H, Arom-H), 8.14 (s, 1H, Arom-H), 7.49-10.15 (s, 1H, NH).

N.B. All compounds were confirmed with LC/MS and showed excellent purities (over 95%).

General

Nuclear magnetic resonance ($^1$HNMR) spectra were obtained on 600 MHz Bruker Advance DPX600 spectrometer at Faculty of Science, King Abdulaziz University using the Me$_4$Si as internal reference and DMSO-d$_6$ or CDCl$_3$ were used as solvents. The chemical shifts were measured in δ ppm.

The reactions were monitored by TLC using Merck precoated silica gel 60F 254 plates. Chemicals are Aldrich, Sigma and Fluka products and are used without further purification.

Melting points were determined with Barnested electrothermal melting point apparatus and are uncorrected. The chemicals, reagents and solvents were purchased from Aldrich chemical company and other international companies through Bayouni/trading companies in Saudi Arabia.

General Procedure for the Synthesis of Monoamide Target Compounds

General method, (Hangauer D G & Al-Zahabi M A 2005): A solution of carboxylic acid IVe (0.01 mol) in $CH_2Cl_2$ (50 ml), was placed in a flask equipped with two dropping funnels and stirred in ice salt bath. A solution of triethylamine TEA (1.5 ml, 0.01 mol) and DMAP (0.122 g, 0.001 mol) in $CH_2Cl_2$ (5 ml) was placed in one of the dropping funnel, and was added to the solution of carboxylic acid (hippuric acid derivatives) while stirring in the ice salt bath, then, ethyl chloroformate (0.12 ml, 0.01 mol) diluted in $CH_2Cl_2$ (5 ml) was placed in the other dropping funnel, and was added in a drop-wise manner over a period of ½ h to the reaction mixture while stirring at ice cooling temperature for 1 h. 3-(Trifluoromethyl)-5,6,7,8-tetrahydro-1,2,4-triazolo[4,3-a]pyrazine hydrochloride (0.01 mol) in water (5 ml) was added portion-wise to the reaction mixture while stirring at the reaction temperature then stirred for additional 2 h at room temperature. The prepared ester was extracted with $CHCl_3$ (30 ml), washed with 5% sodium bicarbonate solution (20 ml) followed by washing with brine (10 ml) and dried over MgSO4. The extract was evaporated under reduced pressure and the obtained solid amide yielded 50-70% yield. N.B. All compounds were confirmed with LC/MS and showed purities >95%.

Biological Screening

Materials and Methods

In Vitro Testing of DPP IV Inhibitory Activity

Sitagliptin phosphate monohydrate and the different tested compounds were dissolved in dimethyl sulphoxide (DMSO) and diluted with tris buffer (pH 8.0, 50 mM) to achieve the required concentrations. DPP-IV inhibition assay was conducted using a kit purchased from Biovision (Milpitas, Calif., USA). Briefly, DPP-IV enzyme was diluted with tris buffer and pipetted 50 µl into glass mini-cells. Subsequently the 25 µl of tris buffer, sitagliptin phosphate monohydrate or the tested compounds was added and incubated at 37° C. for 20 min protected from light. Finally, a volume of 25 µl of DPP-IV substrate was added into each tube. The fluorescence generated from hydrolysis of the substrate was read at Ex/Em=360/460 nm using Modulus® single tube multimode reader (Promega, USA). Baseline fluorescence was recorded before incubation ($R_1$) and 20 min after incubation ($R_2$). Percentage inhibition was calculated according to the following equation:

$$\% \text{ inhibition} = (\Delta\text{RFU test}/\Delta\text{RFU } E_C)*100$$

where, $\Delta\text{RFU} = R_2 - R_1$ and $E_C$ is the enzyme control (enzyme solution without inhibitor) which is considered 100% activity.

The standard DPP-IV inhibitor drug sitagliptin was employed as positive control. Screening was done of all the synthesized compounds at 100 nM then a dose-response study was conducted of the compounds that showed a promising inhibitory effect on DPP-IV activity (>80% inhibition which was comparable to that of sitalgliptin). Sigmoidal dose-response curves for DPP-IV % inhibition versus log concentrations were plotted using Graphpad prism software, version 5.00 (GraphPad Software, Inc. La Jolla, Calif., USA). The $IC_{50}$ value corresponds to the concentration of sample needed to inhibit DPP-IV by 50%.

In Vivo Testing of DPP IV Inhibitory Activity

General Objectives

Our objective was to test the efficacy of the synthesized compounds for their potential to reduce blood glucose in STZ-diabetic mice. The synthesized compounds Nos. 128, 129, 130, 131,140, 142 were expected to act through the inhibition of the DPP-IV enzyme, which is responsible for the degradation of the entero-peptide GLP-I. In turn, GLP-I increases insulin and decreases glucagon release from the pancreatic islets (β and α-cells respectively). So this part of the project was designed to study the effect of the synthesized gliptin simulated compounds on blood glucose levels and their efficacy to increase glucose utilization in diabetic mice through:

a. The effect of the tested compounds in a dose of 50 mg/kg/day on fasting blood glucose blood levels of diabetic mice during six days of treatment.

b. Oral glucose tolerance test (OGTT) through oral glucose loading, 2 h after treatment with single oral dose (50 mg/kg) of the tested compounds in 14 h overnight fasted mice.

c. OGTT through oral glucose loading, 2 h after treatment with the 6th oral dose (50 mg/kg) of the tested compounds in 14 h overnight fasted mice.

d. The effect of the pretreatment with the tested compounds at an oral dose of 50 mg/kg on blood glucose levels, 3 h before and 3 h after meal feeding (feeding for one hour only, then food was removed immediately) in 14 h overnight-fasted diabetic mice.

OGTT after Single Dose

The oral glucose tolerance test was done in 14 h overnight fasted diabetic mice that were pretreated with a single oral dose of the tested compounds. Each of the tested agents was suspended in sodium carboxymethyl cellulose (CMC-Na) (1% in distilled water) and the dosing volume was adjusted to 10 ml/kg body weight per mouse. Then an oral glucose load was administered (2 g/kg) 2 h after drug treatment. Blood glucose levels were determined using the Accu-check Go® (Roche Diagnostics, Michigan, USA). Blood samples were collected just before drug administration (Fasting Blood glucose), then 2 h after drug treatment and before glucose loading. Blood samples collection was continued at 20, 40, 60 and 120 min intervals after glucose loading. The AUC (0-120 min) of the blood glucose levels was calculated by the trapezoidal method.

Animal Groups

Animals were distributed between 17 groups (n=6) as follow:

a. Group 1: Animals were 14 h overnight-fasted normoglycemic mice and vehicle-treated (1% CMC-Na) at a dose of 10 ml/kg.

b. Group 2: Overnight fasted diabetic mice received the vehicle (1% CMC-Na) at a dosing volume of 10 ml/kg and served as a negative control.

c. Group 3: Overnight fasted diabetic mice received sitagliptin at a dose of 50 mg/kg in 1% CMC (in a volume of 10 ml/kg) and served as positive control.

a. Groups 4-17: Animals of these groups were overnight fasted diabetic mice received the tested compounds 128, 129, 130, 131, at a dose of 50 mg/kg in 1% CMC (volume of 10 ml/kg).

OGTT after Multiple Doses of the Tested Compounds:

The tested compounds were given daily by oral gavage for 6 consecutive days. On day 6, the overnight fasted diabetic mice were pretreated with the 6$^{th}$ oral dose of the tested compounds. Then an oral glucose was loaded (2 g/kg/10 ml b.w.) 2 h after drug treatment. Blood glucose levels were determined using the Accu-check Go® (Roche Diagnostics, Michigan, USA). Samples were collected just before drug administration (Fasting Blood glucose), then 2 h after drug treatment and before glucose administration. Sample collection was continued at 20, 40, 60 and 120 min intervals after glucose loading. The AUC (0-120 min) of blood glucose levels was calculated by the trapezoidal method.

Animal Groups:

Animals were distributed between 17 groups (n=6) as follow:
  b. Group 1: Animals of this group are 14 h overnight-fasted normoglycemic mice received the vehicle (1% CMC-Na) at a dosing volume of 10 ml/kg/day for six consecutive days.
  c. Group 2: Overnight-fasted diabetic mice received the vehicle (1% CMC-Na) at a dosing volume of 10 ml/kg/day for six consecutive days and served as a negative control.
  d. Group 3: Overnight-fasted diabetic mice received sitagliptin at a dose of 50 mg/kg/day for six consecutive days and served as positive control.
  e. Groups 4-17: Animals in these groups were overnight-fasted diabetic mice and received the tested compounds 128, 129, 130, 131, at a dose of 50 mg/kg/day for six consecutive days (volume of 10 ml/kg).

Effect on Blood Glucose Level after Introduction of Food for One Hour (≈Meal Tolerance Test)

Rational of the Test

The rational of this test was to determine the ability of the tested compounds to modulate glucose utilization after the introduction of food, after 3 h of drug administration to 14 h overnight-fasted mice (feeding with normal diet was done for 1 hr only, then food was removed during the remaining time of the test). This model is analogous to oral glucose tolerance tests (OGTT) used clinically to evaluate glycemic control, except that the meal was composed of fats, proteins and carbohydrates, and thus was a more realistic representation of the nutritional makeup of normal food. The main purpose is that during meal digestion, food contents e.g. carbohydrates, proteins and fats, were reported to cause an increase in the production of the GLP-I from the L-cells in ileum and colon. The produced GLP-I goes into circulation directly and affects insulin secretion from pancreatic β-cells. Both the GPL-I and insulin levels are expected to be high especially in the presence of a DPP-V inhibitor.

Animal Groups

Animal Groups

Animals were Distributed Between 17 Groups (n=6) as Follows:
  a. Group 1. Animals of this group were overnight-fasted normoglycemic mice and received the vehicle (1% CMC-Na) at a volume of 10 ml/kg/day for 4 consecutive days.
  b. Group 2: overnight-fasted diabetic mice received the vehicle (1% CMC-Na) at a volume of 10 ml/kg/day for 4 consecutive days and served as a negative control.
  c. Group 3: overnight fasted diabetic mice received sitagliptin at a dose of 50 mg/kg/day for 4 consecutive days in 1% CMC (in a volume of 10 ml/kg) and served as positive control.
  d. Groups 4-19: Animals of these groups were overnight-fasted diabetic mice and received the tested compounds 128, 129, 130, 131,140, 142 at a dose of 50 mg/kg/day for 4 consecutive days in 1% CMC (volume of 10 ml/kg). Food was introduced for one hour only then food was removed immediately. Blood glucose levels were determined just before and 3 h after drug administration and then at 0, 60, 120 and 180 min after meal.

Blood Sampling and Blood Glucose Determination

Blood samples were collected from the tail vein and the blood glucose level was determined. Curves of blood glucose levels (mg/dL) versus the time intervals (min) were constructed and the area under the curves (AUCs) were calculated by the method of calculation embedded in Graph-Pad Prism® v. 5.0 (GraphPad Software, San Diego, Calif., USA). AUCs of the curves of the different groups were compared and tested for significance against control groups.

Results of Biological Screening

All data are presented as means±SEM. Statistical significance was evaluated by analysis of variance (ANOVA) followed by Tukey-Kramer's post hoc test for multiple comparisons. The "t" of the paired data was used to test the significance of the values of the fasting blood glucose compared to the values before treatment. Statistical significance was accepted at a level of $p<0.05$.

In-Vitro Inhibitory Effect on DPP-IV Enzyme Activity

Figure 15A:
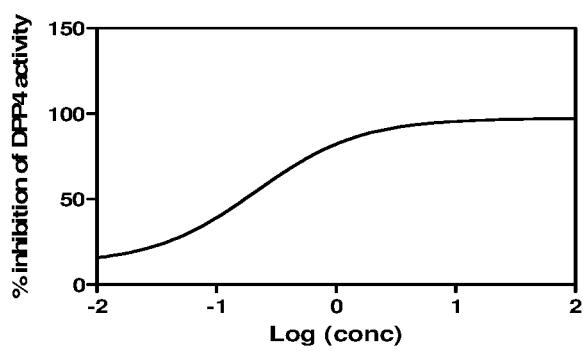
FIG. 15A-C. Graphical presentation of DPP4 activity. A, GLP-130; B, GLP-140; C, GLP-142.
Figure 15B:
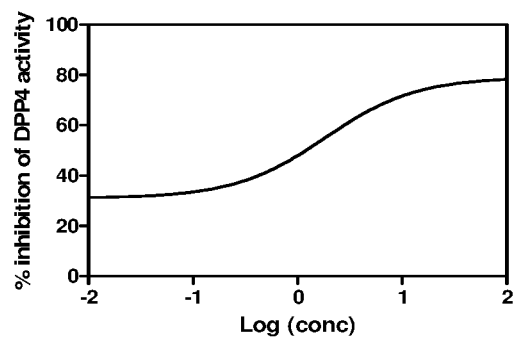
Figure 15C:
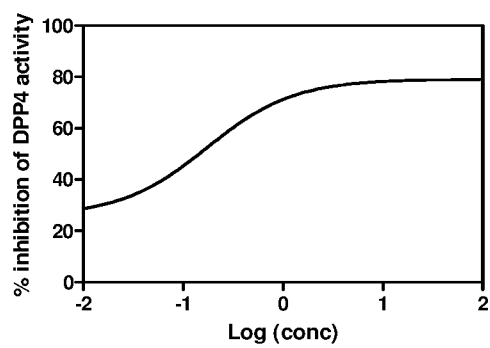

The prepared sitagliptin analogues that passed the preliminary test were subjected to a concentration-inhibition study to determine their $IC_{50}$. Two compounds showed extremely potent activities that were less than 1 nM. The compounds, GLP-142 and GLP-130, showed an $IC_{50}$ of 0.18 and 0.21 nM, respectively. Further, the compound GLP-140, exhibited a parallel activity with an $IC_{50}$ of 1.84 nM respectively. FIGS. 15A-C show a graphical presentation of DPP4 activity corresponding to Table 1.

TABLE 1

Sitagliptin Analogues showing high DPP4-inhibiting potency

| Comp. Code No. | Compound Structure | IC50 |
|---|---|---|
| GLP-130 | 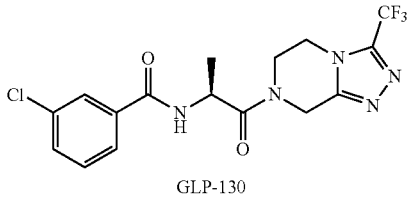 [SMILES: C[C@H](NC(=O)c1cccc(Cl)c1)C(=O)N1CCn2c(nnc2C(F)(F)F)C1] GLP-130 | 0.21 nM |
| GLP-140 | 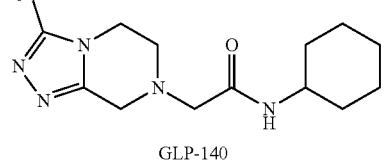 GLP-140 | 1.84 nM |
| GLP-142 | 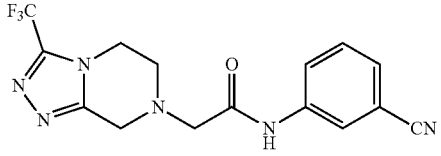 GLP-142 | 0.18 nM |

II In Vivo Effects on Fasting Blood Glucose

The data in Table (2) indicate that all synthesized sitagliptin-related compounds (128, 129, 130, 131, 140 and 142) exhibited significant activity in controlling the rise of blood glucose levels in streptozotocin diabetic animals. The observed effect was consistent over the 6-day interval. In addition, administration of multiple doses of the tested compounds on a daily basis resulted in a further control of fasting blood glucose levels. Compounds 129, 130, 131, 140 and 142 showed obvious potency that was comparable to that of sitagliptin in showing good diabetic control of fasting blood sugar. However, compound GLP-130 and GLP-131 showed the most consistent and extended activities among all tested compounds, including the reference drug sitagliptin. Compound GLP-128 was the least effective in reducing fasting blood glucose.

TABLE 2

Fasting blood glucose of diabetic mice, treated with compounds 128, 129, 130, 131, 140 and 142 (50 mg/kg/day for consecutive 6 days) vs sitagliptin

| | Blood glucose level (mg/dL) | | | | | |
|---|---|---|---|---|---|---|
| | Day 1 | Day 2 | Day 3 | Day 4 | Day 5 | Day 6 |
| Normal control | 80.93* ± 8.64 | 95.60* ± 3.14 | 118.60* ± 5.89 | 108.20* ± 5.29 | 115.60* ± 3.72 | 116.10* ± 28.62 |
| Diabetic control | 200.20 ± 14.52 | 200.00 ± 21.36 | 279.40 ± 23.5 | 257.20 ± 22.39 | 269.60 ± 29.17 | 198.90 ± 34.79 |
| Sitagliptin | 134.40* ± 4.05 | 128.80* ± 12.40 | 109.00* ± 9.06 | 108.20* ± 9.94 | 114.60* ± 3.18 | 96.80* ± 8.78 |
| Compound 128 | 128.00* ± 14.99 | 124.00* ± 17.92 | 177.60* ± 31.98 | 195.00 ± 27.49 | 200.60 ± 23.21 | 188.60 ± 15.86 |
| Compound 129 | 160.20* ± 14.71 | 129.80* ± 20.77 | 126.80* ± 22.49 | 110.80* ± 28.66 | 147.50* ± 41.96 | 136.00* ± 34.47 |
| Compound 130 | 141.40* ± 5.98 | 106.60* ± 15.27 | 106.60* ± 15.27 | 111.20* ± 17.67 | 138.20* ± 17.05 | 113.80* ± 10.18 |
| Compound 131 | 123.40* ± 15.07 | 115.80* ± 9.17 | 114.60* ± 9.80 | 128.40* ± 5.47 | 132.20* ± 7.49 | 113.80* ± 15.75 |
| Compound 140 | 210.0 ± 12.345 | 144.2* ± 17.19 | 139.5* ± 7.334 | 141.2* ± 15.75 | 143.7* ± 12.3 | 150.6* ± 15.939 |
| Compound 142 | 230.0 ± 13.769 | 135.8* ± 7.137 | 153* ± 9.623 | 188.8 ± 25.784 | 205.4 ± 39.315 | 136.6* ± 17.554 |

*Significantly different from corresponding diabetic control group at $p < 0.05$

Effect on Oral Glucose Tolerance:

1-Effect of a Single Dose of the Tested Compounds on Oral Glucose Tolerance Administration of a single dose of the tested compounds, 128, 129, 130, 131, 140 and 142 2 h before glucose loading, leads to variable changes in the total AUC 0-120 of blood glucose levels. Sitagliptin induced 24.2% reduction in the total AUC compared to the diabetic control mice. As shown Table 3, all compounds showed a significant ability to lower glucose levels in this test. In particular, GLP-128, 130 and 131 demonstrated higher glucose-lowering activity than sitagliptin while compounds 129, 140 and 142 were less potent than sitagliptin, and all the tested compounds induced significant reductions in the total AUC of glucose tolerance after glucose loading and were more potent than sitagliptin (see Table 3 and FIGS. 2A-D and FIG. 3). These reductions in the total AUC ranged between 51.88%-29.15% of that of the diabetic control. The tested compounds can be arranged in a descending rank order as follows; 131>130>sitagliptin>142>140 (Table 3). In contrast, compounds 128 and 129 showed the least potency in controlling the rise in blood glucose and consequently AUC.

TABLE 3

Area under the curve in OGTT after oral glucose loading in diabetic mice 2 h pretreated with single dose of compound 128, 129, 130, 131, 140, 142 given orally in a dose of 50 mg/kg each vs sitagliptin

| | AUC (mg · dL$^{-1}$ · min) after single dose treatment | | | | |
|---|---|---|---|---|---|
| Treatment | X | S.E. | Δ from diabetic control | % change from diabetic control | Relative potency to sitagliptin |
| Normal + vehicle | 21067* | 2537 | — | — | — |
| Diabetic control | 51065 | 2216 | — | — | |
| Sitagliptin | 38703* | 2143 | −12362 | −24.20 | 1 |
| Comp-128 | 36178* | 2130 | −14887 | −29.15 | 1.2 |
| Comp-129 | 45480 | 2528 | −5585 | −10.93 | 0.45 |
| Comp-130 | 34720* | 1508 | −16345 | −32.01 | 1.32 |
| Comp-131 | 32230* | 2893 | −18835 | −36.88 | 1.52 |
| Comp-140 | 42439 | 2931 | −8626 | −16.89 | 0.69 |
| Comp-142 | 41613 | 3233 | −9452 | −18.51 | 0.76 |

X = Arithmetic Mean;
S.E. = Standard Error
*Significantly different from the diabetic control group at $p < 0.05$

2—Effect of Multiple Doses on Glucose Tolerance

The effect of treatment with the tested compounds, 128, 129, 130, 131, 140 and 142 for 6 consecutive days on glucose tolerance and glucose utilization was investigated. The results showed that sitagliptin and compounds induced significant reductions in the total area under the curve after oral glucose loading in overnight fasted mice. The percentage reductions were ranged from 52.99 to 11.7 of the diabetic control mice (Table 4). Compounds 130, 131 and 140 showed comparable or higher relative potency than sitagliptin in this test (Table 4 and FIGS. 6A-C and 7A and B).

TABLE 4

Area under the curve in OGTT after oral glucose loading in diabetic mice 2 h pretreated with the tested Compounds 128, 129, 130, 131, 140 and 142 when given orally in a dose of 50 mg/kg each, for six days vs sitagliplin AUC (mg · dL$^{-1}$ · min) after single dose treatment

| Treatment | X | S.E. | Δ from diabetic control | % change from diabetic control | Relative potency to sitagliptin |
|---|---|---|---|---|---|
| Normal + vehicle | 26750* | 2707 | | | |
| Diabetic control | 52655 | 2481 | | | |
| Sitagliptin | 32723 | 2016 | −19932 | −37.85 | 1 |
| Comp-128 | 46368 | 3439 | −6287 | −11.93 | 0.32 |
| Comp-129 | 46458 | 2519 | −6197 | −11.76 | 0.31 |
| Comp-130 | 34672* | 2063 | −17983 | −34.11 | 0.90 |
| Comp-131 | 26542* | 1518 | −26113 | −49.59 | 1.31 |
| Comp-140 | 32475* | 2605 | −20180 | −38.32 | 1.01 |
| Comp-142 | 42439* | 3187 | −10216 | −19.4 | 0.513 |

Figure 13A:
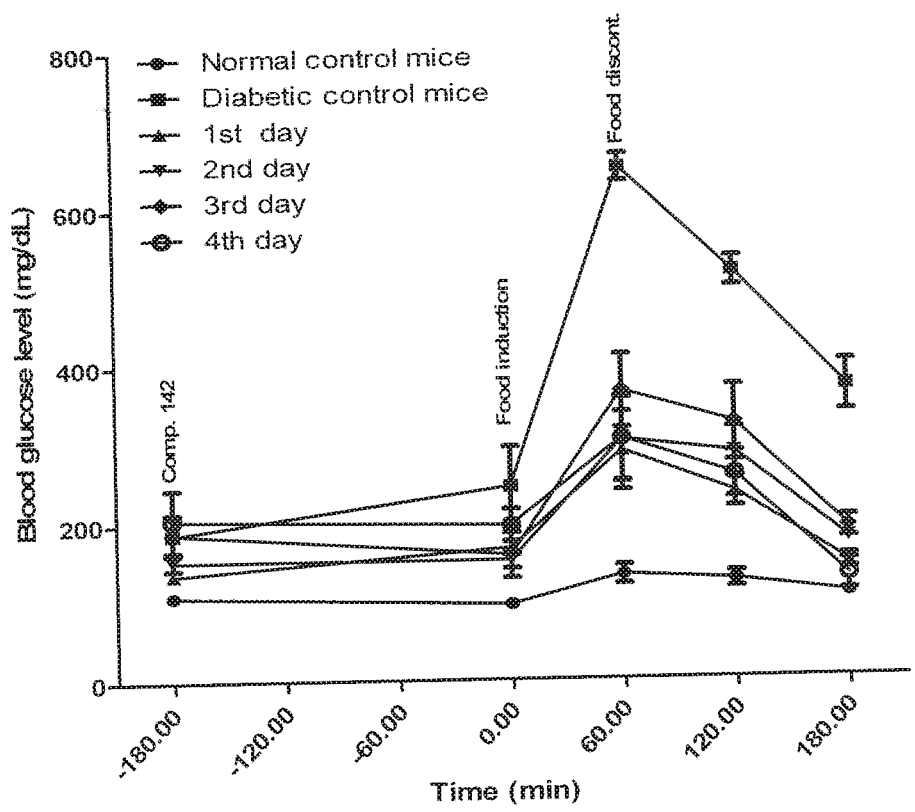
FIGS. 13A and B. Tests of Compound 142 (50 mg/kg) in overnight (14 hr) fasted diabetic mice. A, effect on blood glucose levels during meal feeding (1 hr) and 2 hrs after meal discontinuation during 4 days of treatment; B, blood glucose AUC 0-180 min postmeal feeding 3 hr pretreated. @ indicates a significant difference compared to diabetic control, $P<0.05$.
Figure 13B:
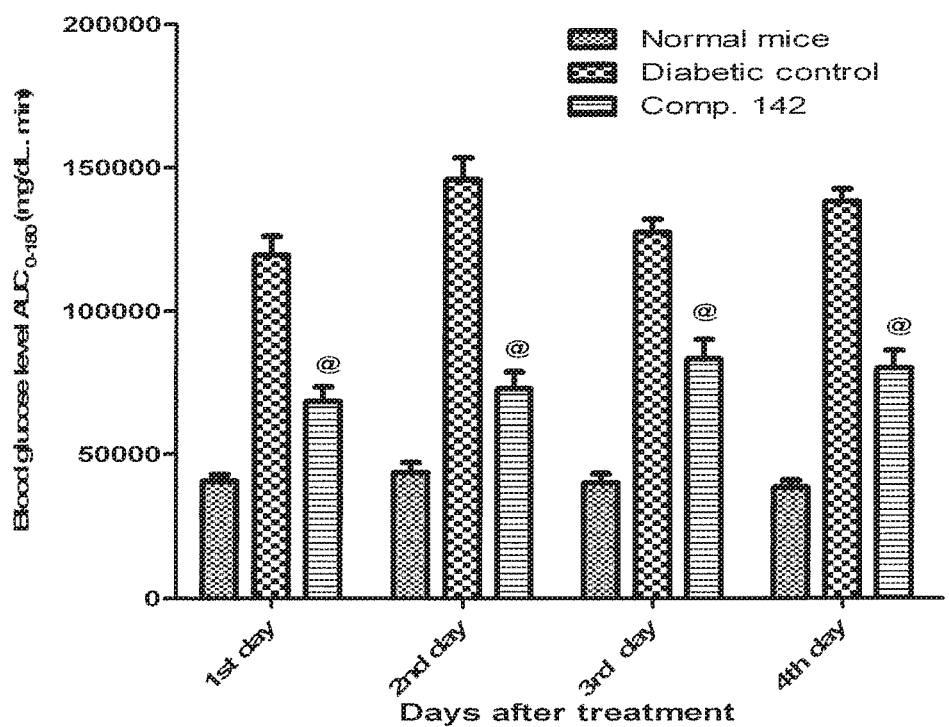
Figure 14A:
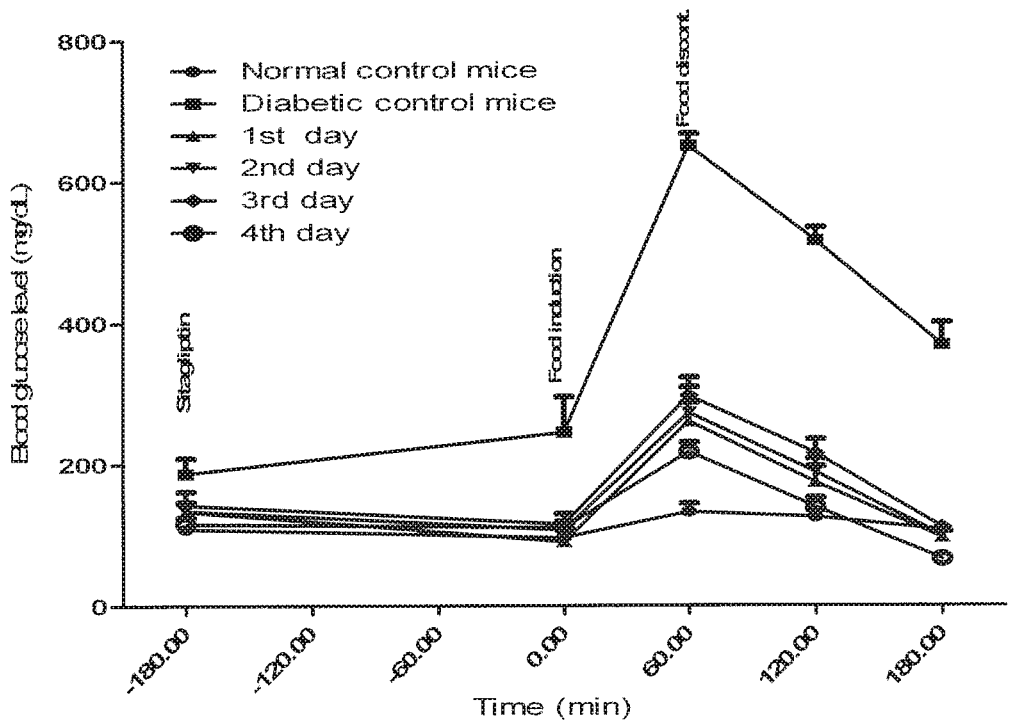
FIGS. 14A and B. Tests of the control, sitagliptin (50 mg/kg) in overnight (14 hr) fasted diabetic mice. A, effect on blood glucose levels during meal feeding (1 hr) and 2 hrs after meal discontinuation during 4 days of treatment; B, blood glucose AUC 0-180 min postmeal feeding 3 hr pretreated. @ indicates a significant difference compared to diabetic control, $P<0.05$.
Figure 14B:
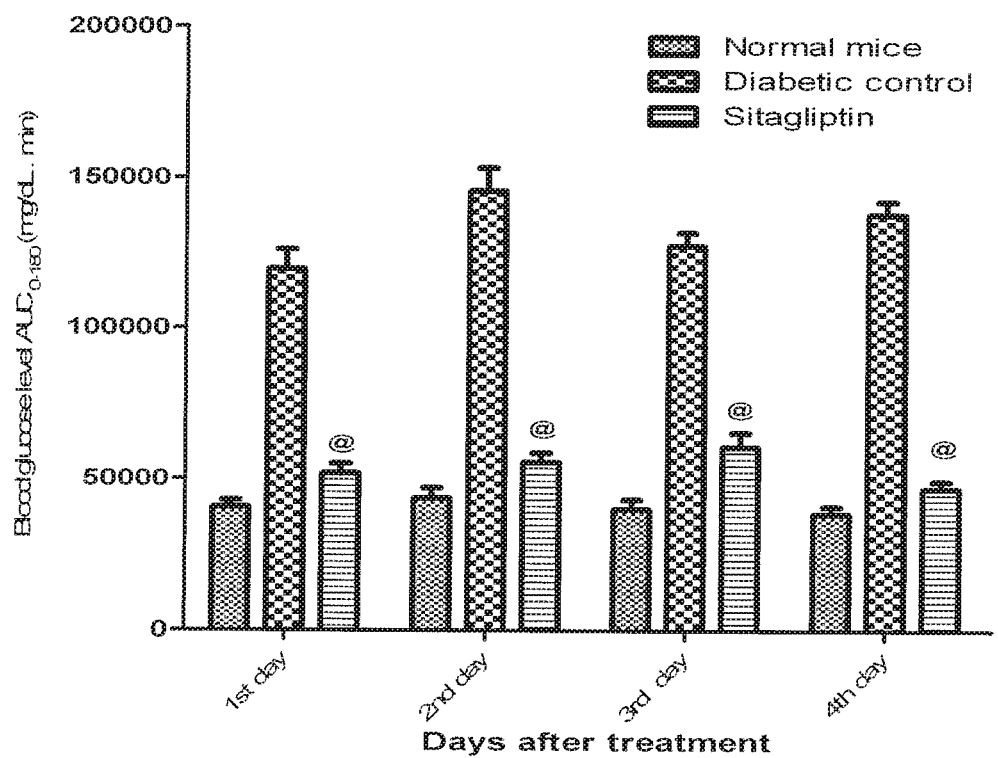

X = Arithmetic Mean;
S.E. = Standard Error
*Significantly different from the diabetic control group at $p < 0.05$ 3-Effect on Blood Glucose after Food Introduction in Overnight Fasted Mice:

Results of the present study showed that introduction of food significantly increased the blood glucose level in both non-diabetic and diabetic overnight fasted mice. The $AUC_{(0-180)}$ after introduction of food were significantly increased. Pretreatment of the diabetic fasted mice with sitagliptin and compounds 128, 129, 130, 131, 140, 142 at a dose of 50 mg/kg each, 3 h before introduction of food, showed significant antihyperglycemic activity that was evidenced by ameliorating the rise in blood glucose levels and the total $AUC_{(0-180)}$. The results are presented in Table 5 for compounds 128, 129, 130, 131, 140, and in FIGS. 7A and B through FIGS. 13A and B for compounds 128, 129, 130, 131, 140 and 142. Control data for sitagliptin is presented in FIGS. 14A and B.

TABLE 5

Area under the curve [$AUC_{(0-180)}$] after meal feeding[†]
to 14 hr overnight fasted diabetic mice,
3 hr pretreated with Compounds 128, 129, 130, 131 and 140
given orally in a dose of 50 mg/kg each vs sitagliptin Area under the curve (mg · dL$^{-1}$ · min) $AUC_{(0-180)}$

| | Day 1 | Day 2 | Day 3 | Day 4 |
|---|---|---|---|---|
| Normal control | 40554* ± 2345 | 43542* ± 3498 | 39942* ± 3215 | 38382* ± 2436 |
| Diabetic control | 119556 ± 6543 | 145596 ± 7648 | 127362 ± 4532 | 137886 ± 4387 |
| Sitagliptin | 51776* ± 3411 | 55538* ± 3055 | 60712* ± 4643 | 46970* ± 2399 |
| Compound 128 | 69336* ± 3170 | 87528* ± 4499 | 96054* ± 6167 | 96666* ± 5197 |
| Compound 129 | 73248* ± 3598 | 70278* ± 5559 | 63426* ± 4799 | 71325* ± 5574 |
| Compound 130 | 50478* ± 3508 | 51600* ± 3983 | 62112* ± 4008 | 55302* ± 3197 |
| Compound 131 | 56340* ± 3003 | 50946* ± 3715 | 61170* ± 3091 | 55854* ± 3046 |
| Compound 140 | 72873* ± 4518 | 71097* ± 5313 | 74190* ± 5798 | 70275* ± 4667 |

*Significantly different from corresponding diabetic control group at $p < 0.05$
[†]Feeding with normal diet was done for 1 hr only, then food was removed during the remaining time of the test.

Summary

This invention discloses non-covalent antidiabetic compounds that inhibit DPP-4. Many compounds showed higher potency than the reference sitagliptin in both in vitro and in vivo tests.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

Funding Information:

This project was funded by the Deanship of Scientific Research (DSR), at King Abdulaziz University, Jeddah, under grant no. (RG-8-166-38). The authors, therefore, acknowledge with thanks DSR for technical and financial support.

We claim:

1. A compound of Formula I:

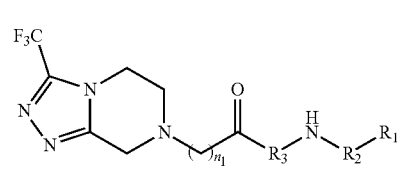

Formula I or a pharmaceutically acceptable salt or stereoisomer thereof,
wherein:
R$_1$ is:
(i) a saturated or unsaturated monocyclic aliphatic ring, wherein the ring is optionally substituted with one or more substituents independently selected from the group consisting of halogen, CN, CH$_3$, CH$_2$CH$_3$, CH(CH$_3$)$_2$, NH(CH$_3$), N(CH$_3$)$_2$, NHC(O)CH$_3$, OH, OCH$_3$, =O, S(O)$_2$CH$_3$, S(O)$_2$NH$_2$, and cyclopropyl;
(ii) a saturated or unsaturated monocyclic aliphatic ring fused with cyclopropane, wherein the ring system is optionally substituted with one or more substituents independently selected from the group consisting of halogen, CN, CH$_3$, CH$_2$CH$_3$, CH(CH$_3$)$_2$, NH(CH$_3$), N(CH$_3$)$_2$, NHC(O)CH$_3$, OH, OCH$_3$, =O, S(O)$_2$CH$_3$, S(O)$_2$NH$_2$, and cyclopropyl;
(iii) a saturated or unsaturated monocyclic aliphatic ring fused with cyclobutene, wherein the ring system is optionally substituted with one or more substituents independently selected from the group consisting of halogen, CN, CH$_3$, CH$_2$CH$_3$, CH(CH$_3$)$_2$, NH(CH$_3$), N(CH₃)₂, NHC(O)CH₃, OH, OCH₃, =O, S(O)₂CH₃, S(O)₂NH₂, and cyclopropyl; or (iv) a monocyclic aromatic ring, wherein the ring is optionally substituted with one or more substituents independently selected from the group consisting of halogen, CN, CH₃, CH₂CH₃, CH(CH₃)₂, NH(CH₃), N(CH₃)₂, NHC(O)CH₃, OH, OCH₃, =O, S(O)₂CH₃, S(O)₂NH₂, and cyclopropyl;

$R_2$ is absent, —CH₂—, —(CH₂)₂—, —(CH₂)₃—, —(CH₂)₄—, —C(O)—, —N(R)—, —NH(CH₂)ₙ—, —S—, —S(O)—, or —S(O)₂—;

$R_3$ is absent, —CH₂—, —(CH₂)₂—, —(CH₂)₃—, —(CH₂)₄—, —N(R)—, —NH(CH₂)ₙ—, —S—, —S(O)—, or —S(O)₂—;

each R is independently H, CH₃, or CH₂CH₃;

each n is independently 1, 2, 3, or 4; and $n_1$ is 1 or 2.

2. A pharmaceutical composition comprising the compound of claim 1, or a pharmaceutically acceptable salt or stereoisomer thereof, and a pharmacologically suitable carrier.

3. A compound selected from the group consisting of:

GLP 128

GLP 129

GLP 130

GLP 131

GLP 136

GLP 138

GLP 139

GLP 140

GLP 142 or a pharmaceutically acceptable salt thereof.

4. The compound of claim 3, wherein the compound is:

GLP 128 or a pharmaceutically acceptable salt thereof.

5. The compound of claim 3, wherein the compound is:

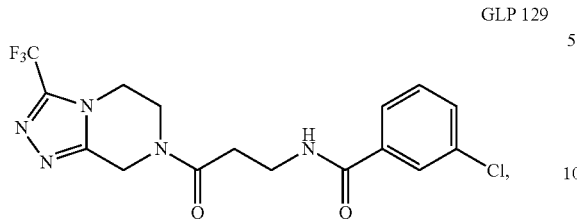

GLP 129 or a pharmaceutically acceptable salt thereof.

6. The compound of claim 3, wherein the compound is:

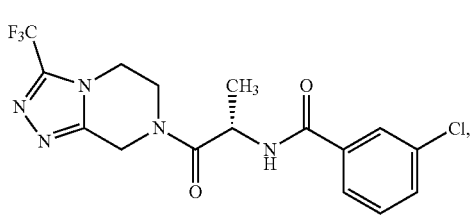

GLP 130 or a pharmaceutically acceptable salt thereof.

7. The compound of claim 3, wherein the compound is:

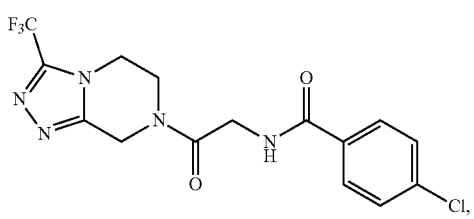

GLP 131 or a pharmaceutically acceptable salt thereof.

8. The compound of claim 3, wherein the compound is:

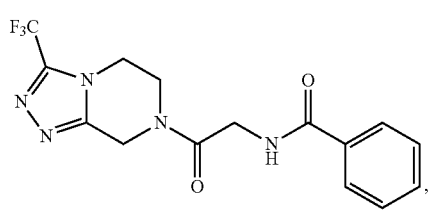

GLP 136 or a pharmaceutically acceptable salt thereof.

9. The compound of claim 3, wherein the compound is:

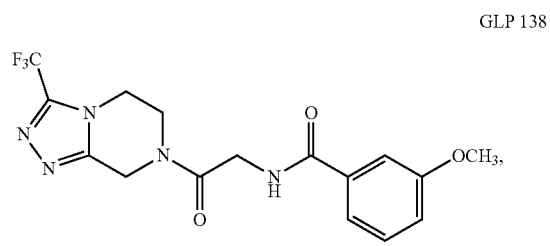 [SMILES: COc1cccc(C(=O)NCC(=O)N2CCn3c(nnc3C(F)(F)F)C2)c1]

GLP 138 or a pharmaceutically acceptable salt thereof.

10. The compound of claim 3, wherein the compound is:

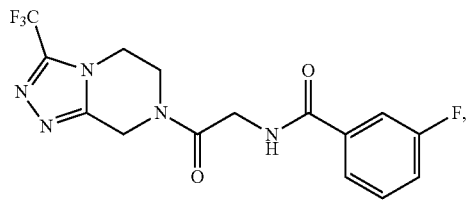

GLP 139 or a pharmaceutically acceptable salt thereof.

11. The compound of claim 3, wherein the compound is:

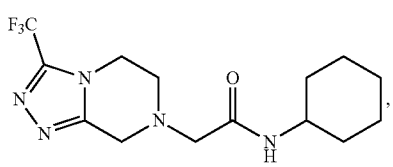

GLP 140 or a pharmaceutically acceptable salt thereof.

12. The compound of claim 3, wherein the compound is:

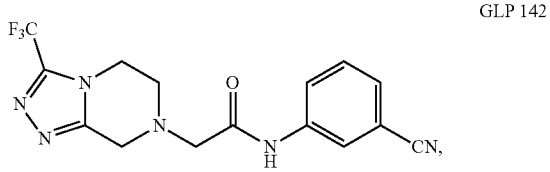 [SMILES: N#Cc1cccc(NC(=O)CN2CCn3c(nnc3C(F)(F)F)C2)c1]

GLP 142 or a pharmaceutically acceptable salt thereof.

13. A pharmaceutical composition comprising the compound of claim 3, or a pharmaceutically acceptable salt thereof, and a pharmacologically suitable carrier.

14. A method for treating hyperglycemia in a subject, comprising administering to the subject in need thereof a therapeutically effective amount of a compound selected from the group consisting of:

GLP 128
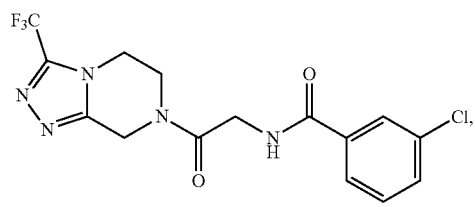
GLP 129
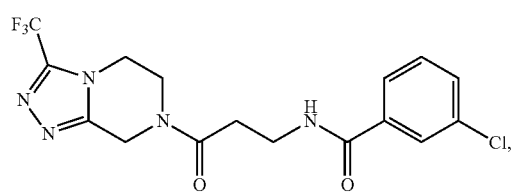
GLP 130
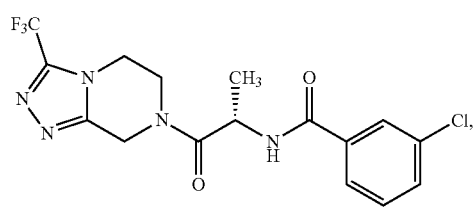
GLP 131
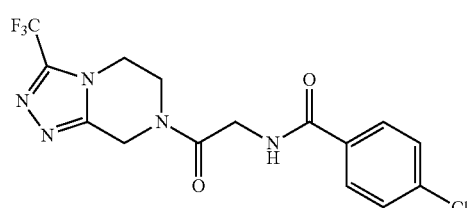
GLP 136
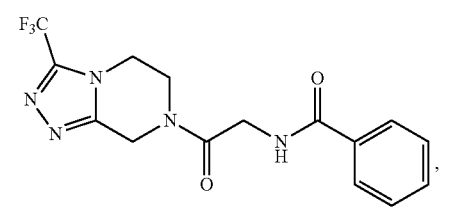
GLP 138
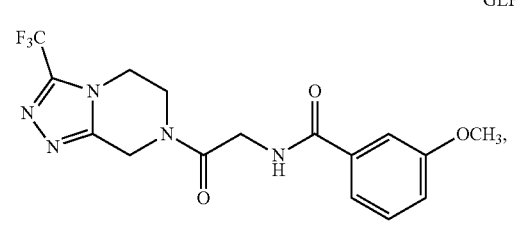
GLP 139
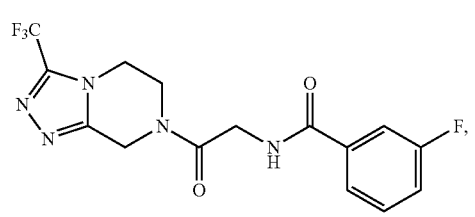
-continued
GLP 140
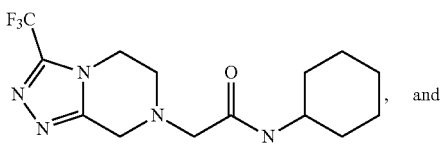
, and
GLP 142
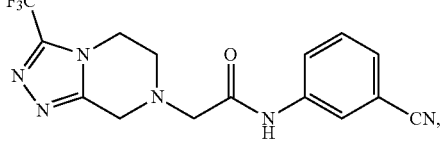
or a pharmaceutically acceptable salt thereof.
15. The method of claim 14, wherein the subject has type II diabetes.
16. The method of claim 14, wherein the compound is selected from the group consisting of:
GLP 128
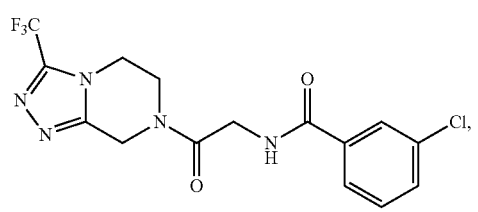
GLP 129
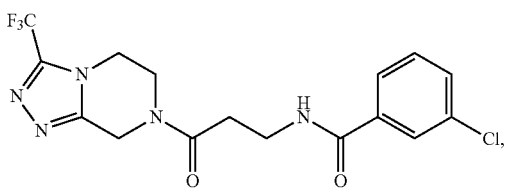
GLP 130
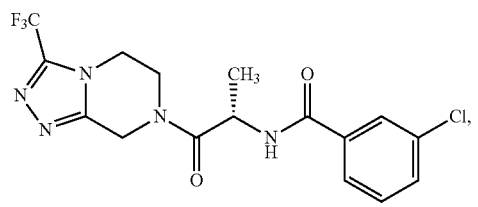
GLP 131
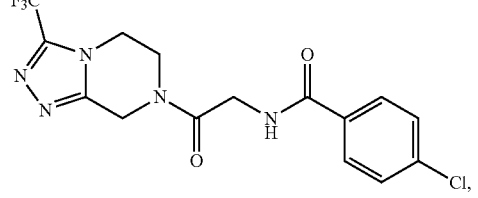
GLP 140
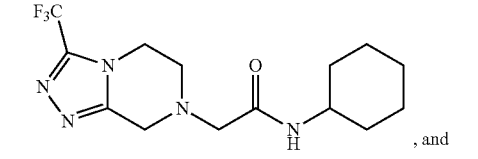
, and GLP 142
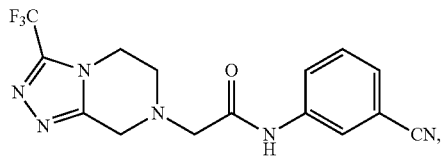
or a pharmaceutically acceptable salt thereof.
* * * * *